United States Patent [19]
Wittman et al.

[11] Patent Number: 5,912,264
[45] Date of Patent: Jun. 15, 1999

[54] 6-HALO-OR NITRATE-SUBSTITUTED PACLITAXELS

[75] Inventors: Mark D. Wittman, Cheshire; John F. Kadow, Wallingford, both of Conn.

[73] Assignee: Bristol-Myers Squibb Company, Princeton, N.J.

[21] Appl. No.: 09/017,344

[22] Filed: Feb. 2, 1998

Related U.S. Application Data

[60] Provisional application No. 60/038,132, Mar. 3, 1997.
[51] Int. Cl.$^6$ ........................ A61K 31/335; C07D 305/14
[52] U.S. Cl. .......................... 514/449; 549/510; 549/511
[58] Field of Search ............................. 514/449; 549/510, 549/511

[56] References Cited

U.S. PATENT DOCUMENTS

| | | | |
|---|---|---|---|
| 4,814,470 | 3/1989 | Colin et al. | 514/449 |
| 4,960,790 | 10/1990 | Stella et al. | 514/449 |
| 5,175,315 | 12/1992 | Holton | 549/510 |
| 5,229,526 | 7/1993 | Holton | 549/213 |
| 5,254,580 | 10/1993 | Chen et al. | 514/449 |
| 5,272,171 | 12/1993 | Ueda et al. | 514/449 |
| 5,352,806 | 10/1994 | Gunawardana et al. | 549/510 |
| 5,380,751 | 1/1995 | Chen et al. | 514/449 |
| 5,395,850 | 3/1995 | Roth | 514/471 |

FOREIGN PATENT DOCUMENTS

| | | |
|---|---|---|
| 590267 A2 | 4/1994 | European Pat. Off. . |
| 600517 A1 | 6/1994 | European Pat. Off. . |
| 764643A1 | 3/1997 | European Pat. Off. . |
| WO93/06093 | 4/1993 | WIPO . |
| WO94/08984 | 4/1994 | WIPO . |
| WO94/20485 | 9/1994 | WIPO . |
| WO94/29288 | 12/1994 | WIPO . |
| WO96/03394 | 2/1996 | WIPO . |

OTHER PUBLICATIONS

E. K. Rowinsky and R. C. Donehower, "The Clinical Pharmacology and Use of Antimicrotubule Agents in Cancer Chemotherapeutics," Pharmac. Ther., 52: 35–84, 1991.
C. M. Spencer and D. Faulds, "Paclitaxel, A Review of its Pharmacodynamic and Pharmacokinetic Properties and Therapeutic Potential in the Treatment of Cancer," Drugs, 48(5), 794–847, 1994.
K. C. Nicolaou, et al, "Chemistry and Biology of Taxol," Angew. Chem., Int. Ed. Engl., 33: 15–44, 1994.
Greene and Wuts, Protective Groups In Organic Synthesis, 2nd Ed., John Wiley & Sons, and McOmie, 1991.
Protective Groups In Organic Chemistry, Ed. J.F.W. McOmie, Plenum Press, 1973.
R.A. Johnson, "Taxol Chemistry. 7–O–Triflates as Precursors to Olefins and Cyclopropanes," Tetrahedron Letters, vol. 35, No. 43, pp. 7893–7896, 1994.
X. Liang and G.I. Kingston, "Synthesis and Biological Evaluation of Paclitaxel Analogs Modified in Ring C," Tetrahedron Letters, vol. 36, No. 17, pp. 2901–2904, 1995.
G. Roth, et al, "Reaction of Paclitaxel and 10–Desacetyl Baccatin III with Diethylamino Sulfurtrifluoride," Tetrahedron Letters, vol. 36, No. 10, pp. 1609–1612, 1995.
S.–H. Chen, et al, "The Chemistry of Taxanes: Reaction of Taxol and Baccatin Derivatives with Lewis Acids in Aprotic and Protic Media," Tetrahedron, vol. 49, No. 14, pp. 2805–2828, 1993.
L.L. Klein, "Synthesis of 9–Dihydrotaxol: A Novel Bioactive Taxane," Tetrahedron Letters, vol. 34, No. 13, pp. 2047–2050, 1993.
Physician's Desk Reference, 49th Edition, Medical Economics, p. 682, 1995.
S.G. Arbuck, et al, Taxol® Science And Applications, edited by M. Suffness, 1995 (CRC Press Inc., Boca Raton, Florida), pp. 379–415.
G. I. Georg, et al, "Stereoselective Synthesis of 9β–Hydroxytaxanes Via Reduction With Samarium Diiodide," Tetrahedron Letters, 36(11), pp. 1783–1786, 1995.
F.A. Holmes, et al, Taxane Anticancer Agents Basic Science and Current Status, edited by G.I. Georg, et al, 1995, American Chemical Society, Washington, D.C. 31–57.
W. Rose, "Evaluation of Madison 109 Lung Carcinoma as a Model for Screening Antitumor Drugs," Cancer Treatment Reports, 65, No. 3–4, pp. 299–312, 1981.
T.L. Riss, et al, "Comparison of MTT, XTT and a Novel Tetrazolium Compound MTS for In–Vitro Proliferation and Chemosensitivity Assays," Mol. Biol. Cell 3 (Suppl.), 184a, 1992.
X. Liang, et al, "Synthesis, Structure Elucidation and Biological Evaluation of C–Norpaclitaxel," Tetrahedron Letters, 36(43), pp. 7795–7798, 1995.
A. G. Chaudhary, et al, "Modified Taxols. Preparation of 7–Deoxytaxol, a Highly Bioactive Taxol Derivative, and Interconversion of Taxol and 7–epi–Taxol," J. Org. Chem., 58, pp. 3798–3799, 1993.

*Primary Examiner*—Ba K. Trinh
*Attorney, Agent, or Firm*—Samuel J. DuBoff

[57] ABSTRACT

The present invention concerns novel taxane derivatives, their use as antitumor agents, and pharmaceutical formulations.

10 Claims, No Drawings

6-HALO-OR NITRATE-SUBSTITUTED PACLITAXELS

This application claims the priority benefit of provisional application No. 60/038,132, dated Mar. 3, 1997.

BACKGROUND OF THE INVENTION

1. Field of the Invention

The present invention concerns antitumor compounds. More particularly, the invention provides novel paclitaxel derivatives, pharmaceutical formulations thereof, and their use as antitumor agents.

2. Background Art

Taxol® (paclitaxel) is a natural product extracted from the bark of Pacific yew trees, Taxus brevifolia. It has been shown to have excellent antitumor activity in in vivo animal models, and recent studies have elucidated its unique mode of action, which involves abnormal polymerization of tubulin and disruption of mitosis. It has recently been approved for the treatment of refractory advanced ovarian cancer and breast cancer; and studies involving other cancers have shown promising results. The results of paclitaxel clinical studies are reviewed by numerous authors, such as by Rowinsky and Donehower in "The Clinical Pharmacology and Use of Antimicrotubule Agents in Cancer Chemotherapeutics," Pharmac. Ther., 52:35–84, 1991; by Spencer and Faulds in "Paclitaxel, A Review of its Pharmacodynamic and Pharmacokinetic Properties and Therapeutic Potential in the Treatment of Cancer," Drugs, 48 (5) 794–847, 1994; by K. C. Nicolaou et al. in "Chemistry and Biology of Taxol," Angew. Chem.. Int. Ed. Engl. 33: 15–44, 1994; by F. A. Holmes, A. P. Kudelka, J. J. Kavanaugh, M. H. Huber, J. A. Ajani, V. Valero in the book "Taxane Anticancer Agents Basic Science and Current Status" edited by Gunda I. Georg, Thomas T. Chen, Iwao Ojima, and Dolotrai M. Vyas, 1995, American Chemical Society, Washington, DC, 31–57; by Susan G. Arbuck and Barbara Blaylock in the book "TAXOL® Science and Applications" edited by Mathew Suffness, 1995, CRC Press Inc., Boca Raton, Fla., 379–416; and also in the references cited therein.

A semi-synthetic analog of paclitaxel named Taxotere® (docetaxel) has also been found to have good antitumor activity. The structures of paclitaxel and Taxotere® are shown below along with the conventional numbering system for molecules belonging to the class; such numbering system is also employed in this application.

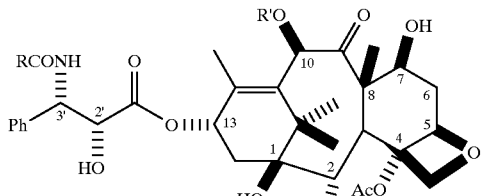

Taxol: R = Ph; R' = acetyl
Taxotere: R = t-butoxy; R' = hydrogen

SUMMARY OF THE INVENTION

This invention relates to novel antitumor compounds represented by formula I, or pharmaceutically acceptable salts thereof

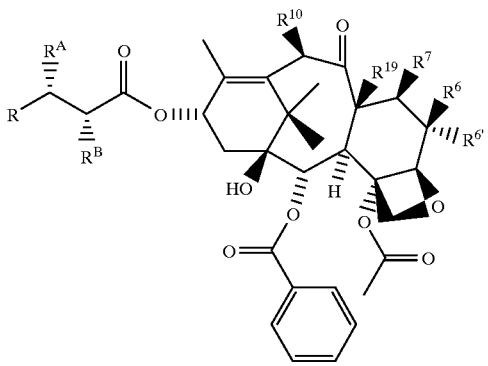

wherein R is hydrogen, $C_{1-6}$ alkyl, $C_{2-6}$ alkenyl, $C_{2-6}$ alkynyl, $C_{3-6}$ cycloalkyl, $C_{3-6}$ cycloalkenyl, cyclic 3–7 membered ring containing either one or two heteroatoms, heteroaryl or —$Z^1$—$R^3$;

$Z^1$ is a direct bond, $C_{1-6}$ alkyl, or —O—$C_{1-6}$ alkyl;

$R^3$ is aryl, substituted aryl, $C_{3-6}$ cycloalkyl, $C_{3-6}$ cycloalkenyl, cyclic 3–7 membered ring containing either one or two heteroatoms, or heteroaryl;

$R^A$ is —NHC(O)R, —NHC(O)OR, —NHC(O)NHR, —NHC(O)N(R)$_2$, —NHS(O)$_m$R, —NHP(=O)(OR)$_2$, —NHP=S(OR)$_2$, where m is 1 or 2;

$R^B$ is hydroxy, fluoro, —OC(O)R$^x$, —OC(O)OR$^x$, OP(O)(OH)$_2$, OCH$_2$OP(O)(OH)$_2$, —OCH$_2$OCH$_2$OP(=O)(OH)$_2$, OP(O)(OH)$_2$ base, OCH$_2$OP(O)(OH)$_2$ base, —OCH$_2$OCH$_2$OP(=O)(OH)$_2$ base, —(OCH$_2$)$_m$OC=OCH$_2$NHR$^x$, —(OCH$_2$)$_m$OC(=O)CH(R")NR'$_6$R'$_7$ where m is 0–3, —OCOCH$_2$CH$_2$NH$_3^+$ HCOO$^-$, —OCOCH$_2$CH$_2$COOH, —OCO(CH$_2$)$_3$COOH,— OC(O)(CH$_2$)$_n$NR$^F$R$^G$, where n is 0–3, —OC(O)CH$_2$CH$_2$C(O)OCH$_2$CH$_2$OH or —OC(O)—Z—C(O)—R';

Z is ethylene (—CH$_2$CH$_2$—), propylene (—CH$_2$CH$_2$CH$_2$—), —CH=CH—, 1,2-cyclohexane or 1,2-phenylene;

R' is —OH, —OH base, —NR'$_2$R'$_3$, —OR'$_3$, —SR'$_3$, or —OCH$_2$C(O)NR'$_4$R'$_5$;

R'$_2$ is —H or —CH$_3$;

R'$_3$ is —(CH$_2$)$_n$R'$_6$R'$_7$ or (CH$_2$)$_n$N$^+$R'$_6$R'$_7$R'$_8$X$^-$, where n is 1–3;

R'$_4$ is —H or —C$_1$–C$_4$ alkyl;

R'$_5$ is —H, —C$_1$–C$_4$ alkyl, benzyl, hydroxyethyl, —CH$_2$C O$_2$H or dimethylaminoethyl;

R'$_6$ and R'$_7$ are independently —H, —CH$_3$, —CH$_2$CH$_3$, benzyl or R'$_6$ and R'$_7$ together with the nitrogen of NR'$_6$R'$_7$ form a pyrrolidino, piperidino, morpholino, or N-methylpiperizino group;

R'$_8$ is —CH$_3$, —CH$_2$CH$_3$ or benzyl;

X$^-$ is halide;

base is NH$_3$, (HOC$_2$H$_4$)$_3$N, N(CH$_3$)$_3$, CH$_3$N(C$_2$H$_4$)$_2$NH, NH$_2$(CH$_2$)$_6$NH$_2$, N-methylglucamine, NaOH or KOH;

R$^F$ and R$^G$ are independently —H or —C$_1$–C$_3$ alkyl, or R$^F$ and R$^G$ taken together with the nitrogen of NR$^F$R$^G$ form a pyrrolidino, piperidino, morpholino or N-methylpiperizino groups;

R" is —H, —CH$_3$, —CH$_2$CH(CH$_3$)$_2$, —CH(CH$_3$)CH$_2$CH$_3$, —CH(CH$_3$)$_2$, —CH$_2$phenyl, —(CH$_2$)$_3$NH$_2$, —(CH$_2$)$_4$NH$_2$, —CH$_2$CH$_2$COOH, —(CH$_2$)$_3$NHC(=NH)NH$_2$, the residue of the amino acid proline, —OC(O)CH=CH$_2$, —C(O)CH$_2$CH$_2$C(O)NHCH$_2$CH$_2$SO$_3$—Y+ or —OC(O)CH$_2$CH$_2$C(O)NHCH$_2$CH$_2$CH$_2$SO$_3$—Y+;

Y+ is Na+ or N+(Bu)$_4$;

$R^6$ and $R^{6'}$ are independently fluoro, chloro, bromo, iodo or $ONO_2$ with the proviso that one of $R^6$ or $R^{6'}$ is hydrogen;

$R^7$ is hydrogen, hydroxy, —O—$C_{1-6}$ alkyl, —OC(O)$R^x$, —OC(O)O$R^x$, —OC(O)NH$R^x$, —OC(O)NR'$_6$R'$_7$, —OCH$_2$OR, —OC($R^x$)$_2$OR, —OCHR$^x$OR, —OCH$_2$OCH$_2$SCH$_3$, OP(O)(OH)$_2$, OCH$_2$OP(O)(OH)$_2$, —OCH$_2$OCH$_2$OP(O)(OH)$_2$, —(OCH$_2$)$_n$OC=OCH$_2$NHR$^x$, —(OCH$_2$)$_n$OC(=O)CH(R")NR'$_6$R'$_7$, where n is 0–3, OCH$_2$SR, —OC($R^x$)$_2$SR, —OCHR$^x$SR, —OCOCH$_2$CH$_2$NH$_3^+$ HCOO$^-$, —OCOCH$_2$CH$_2$COOH, —OCO(CH$_2$)$_3$COOH,—OC(O)(CH$_2$)$_n$NR$^F$R$^G$, where n is 0–3, —OC(O)—Z—C(O)—R', —OC(O)CH$_2$CH$_2$C(O)OCH$_2$CH$_2$OH or when taken together with $R^{19}$ forms a cyclopropane ring;

$R^{19}$ is methyl or when taken together with $R^7$ forms a cyclopropane ring;

$R^{10}$ is hydrogen, hydroxy, —OC(O)$R^x$, —OC(O)O$R^x$, —O—$C_{1-6}$ alkyl, —OCH$_2$OCH$_3$, —OCH$_2$OCH$_2$OCH$_3$, —OCH$_2$OCH$_2$OCH$_2$CH$_3$, —OCH$_2$OCH$_2$CH$_2$OCH$_3$, —OCH$_2$OCH$_2$CH$_2$OH, —OCH$_2$SR, —OCH$_2$OCH$_2$SCH$_3$, —OC(O)NR'$_6$R'$_7$, $C_{1-6}$ alkyl, —(CH$_2$)$_3$C(O)$R^x$, —(CH$_2$)$_3$C(O)O$R^x$, —(CH$_2$)$_3$CN,—OP(O)(OH)$_2$, —OCH$_2$OP(O)(OH)$_2$, —OCH$_2$OCH$_2$OP(O)(OH)$_2$, —(OCH$_2$)$_n$OC=OCH$_2$NHR$^x$, —(OCH$_2$)$_n$OC(=O)CH(R")NR'$_6$R'$_7$, where n is 0–3, —OCOCH$_2$CH$_2$NH$_3^+$ HCOO$^-$, —OCOCH$_2$CH$_2$COOH,—OCO(CH$_2$)$_3$COOH,—OC(O)—Z—C(O)—R', —OC(O)(CH$_2$)$_n$NR$^F$R$^G$ where n is 0–3, or —OC(O)CH$_2$CH$_2$C(O)OCH$_2$CH$_2$OH; and $R^x$ is $C_{1-6}$ alkyl, $C_{2-6}$ alkenyl, $C_{2-6}$ alkynyl, $C_{3-6}$ cycloalkyl, any of which groups can be optionally substituted with one to six of the same or different halogen atoms or with one or more hydroxy groups.

Another aspect of the present invention provides a method for inhibiting tumor in a mammalian host which comprises administering to said mammalian host an antitumor effective amount of a compound of formula I.

Yet, another aspect of the present invention provides a pharmaceutical formulation which comprises an antitumor effective amount of a compound of formula I in combination with one or more pharmaceutically acceptable carriers, excipients, diluents or adjuvants.

DETAILED DESCRIPTION

In the application, unless otherwise specified explicitly or in context, the following definitions apply. The numbers in the subscript after the symbol "C" define the number of carbon atoms a particular group can contain. For example "$C_{1-6}$ alkyl" means a straight or branched saturated carbon chain having from one to six carbon atoms; examples include methyl, ethyl, n-propyl, isopropyl, n-butyl, sec-butyl, isobutyl, t-butyl, n-pentyl, sec-pentyl, isopentyl, and n-hexyl. Depending on the context, "$C_{1-6}$ alkyl" can also refer to $C_{1-6}$ alkylene which bridges two groups; examples include propane-1,3-diyl, butane-1,4-diyl, 2-methyl-butane-1,4-diyl, etc. "$C_{2-6}$ alkenyl" means a straight or branched carbon chain having at least one carbon-carbon double bond, and having from two to six carbon atoms; examples include ethenyl, propenyl, isopropenyl, butenyl, isobutenyl, pentenyl, and hexenyl. Depending on the context, "$C_{2-6}$ alkenyl" can also refer to $C_{2-6}$ alkenediyl which bridges two groups; examples include ethylene-1,2-diyl (vinylene), 2-methyl-2-butene-1,4-diyl, 2-hexene-1,6-diyl, etc. "$C_{2-6}$ alkynyl" means a straight or branched carbon chain having at least one carbon-carbon triple bond, and from two to six carbon atoms; examples include ethynyl, propynyl, butynyl, and hexynyl.

"Aryl" means aromatic hydrocarbon having from six to ten carbon atoms; examples include phenyl and naphthyl.

"Substituted aryl" means aryl independently substituted with one to five (but preferably one to three) groups selected from $C_{1-6}$ alkanoyloxy, hydroxy, halogen, $C_{1-6}$ alkyl, trifluoromethyl, $C_{1-6}$ alkoxy, aryl, $C_{2-6}$ alkenyl, $C_{1-6}$ alkanoyl, nitro, amino, cyano, azido, $C_{1-6}$ alkylamino, di-$C_{1-6}$ alkylamino, and amido. "Halogen" means fluorine, chlorine, bromine, and iodine.

"Heteroaryl" means a five- or six-membered aromatic ring containing at least one and up to four non-carbon atoms selected from oxygen, sulfur and nitrogen. Examples of heteroaryl include thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, and like rings.

"Hydroxy protecting groups" include, but is not limited to, ethers such as methyl, t-butyl, benzyl, p-methoxybenzyl, p-nitrobenzyl, allyl, trityl, methoxymethyl, methoxyethoxymethyl, ethoxyethyl, tetrahydropyranyl, tetrahydrothiopyranyl, dialkylsilylethers, such as dimethylsilyl ether, and trialkylsilyl ethers such as trimethylsilyl ether, triethylsilyl ether, and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates such as methyl, ethyl, 2,2,2-trichloroethyl, allyl, benzyl, and p-nitrophenyl. Additional examples of hydroxy protecting groups may be found in standard reference works such as Greene and Wuts, *Protective Groups in Organic Synthesis*, 2d Ed., 1991, John Wiley & Sons, and McOmie; and *Protective Groups in Organic Chemistry*, 1975, Plenum Press.

"Ph" means phenyl; "ipr" means isopropyl; "DAST" means diethylamino sulfur trifluoride.

The substituents of the substituted alkyl, alkenyl, alkynyl, aryl, and heteroaryl groups and moieties described herein, may be alkyl, alkenyl, alkynyl, aryl, heteroaryl and/or may contain nitrogen, oxygen, sulfur, halogens and include, for example, lower alkoxy such as methoxy, ethoxy, butoxy, halogen such as chloro or fluoro, nitro, amino, and keto.

A preferred embodiment are compounds with the structure I, or pharmaceutically acceptable salts thereof, having the following groups:

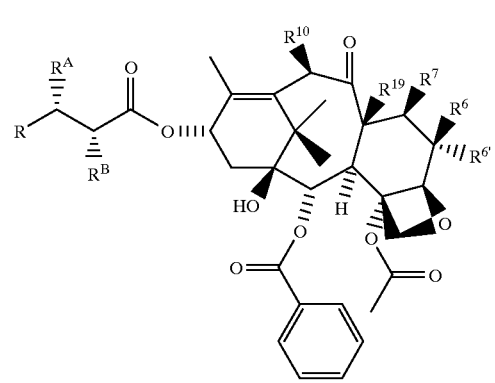

I

R includes 2-furanyl (2-furyl), 2-thienyl, 3-furanyl (3-furyl), 3-thienyl, phenyl, napthyl, 4-hydroxyphenyl, 4-methoxyphenyl, 4-fluorophenyl, 4-trifluoromethylphenyl, 2-propynyl, benzyl, phenethyl, phenylethenyl, 3,4-dimethoxyphenyl, 2-(2-furanyl)ethenyl, 2-methylpropyl, $C_{3-6}$ cycloalkyl, cyclohexylmethyl, cyclohexylethyl and the like.

R also includes $C_{3-6}$ alkyl including n- propyl, n-butyl, sec-butyl, isopropyl, 2-methyl-propyl, isobutyl, $C_{3-6}$ alkenyl including 1-(1-propenyl), 1-(2-propenyl),2-propenyl, 2-(1-butenyl), 1-(2-butenyl), 1-(3-butenyl), 2-(1-butenyl), 2-(2-butenyl), 2-(3-butenyl),and 1-(2-methyl-1-propenyl) (isobutenyl), t-butyl, or —$Z^1$—$R^3$; $Z^1$ is a direct bond; $R^3$ is aryl including phenyl, substituted aryl including p fluoro phenyl and p-methyl phenyl, $C_{3-6}$ cycloalkyl including cyclopropyl, cyclobutyl, cyclopentyl, and cyclohexyl, $C_{3-6}$ cycloalkenyl, cyclic 3–7 membered ring containing either one or two heteroatoms, or heteroaryl such as 2-furyl, 3-furyl, 2-thienyl, or 3-thienyl.

$R^A$ includes —NHC(O)Ph (or substituted phenyl) —NHC(O)O($C_{1-6}$ alkyl), most preferably —NHC(O)OtBu, —NHC(O)OnBu, —NHC(O)OiPr, —NHC(O)OCH$_2$Ph, —NHC(O)OMe, —NHC(O)OEt, —NHC(O)OnPr, NHC(O)-heterocycle, including —NHC(O)-2-furyl, —NHC(O)NHR, —NHC(O)N(R)$_2$;

$R^B$ is hydroxy, fluoro, —OC(O)$R^x$, —OC(O)O$R^x$, OP(O)(OH)$_2$, OCH$_2$OP(O)(OH)$_2$, —OCH$_2$OCH$_2$OP(=O)(OH)$_2$, OP(O)(OH)$_2$ base, OCH$_2$OP(O)(OH)$_2$ base, —OCH$_2$OCH$_2$OP(=O)(OH)$_2$ base, —(OCH$_2$)$_m$OC=OCH$_2$NHR$^x$, —(OCH$_2$)$_m$OC(=O)CH(R")NR'$_6$R'$_7$ where m is 0–3, —OCOCH$_2$CH$_2$NH$_3^+$ HCOO$^-$, —OCOCH$_2$CH$_2$COOH, —OCO(CH$_2$)$_3$COOH,—OC(O)(CH$_2$)$_n$NR$^F$R$^G$, where n is 0–3, —OC(O)CH$_2$CH$_2$C(O)OCH$_2$CH$_2$OH or —OC(O)—Z—C(O)—R';

$R^6$ and $R^{6'}$ are independently fluoro, chloro, bromo, iodo or ONO$_2$ with the proviso that one is hydrogen;

$R^7$ is hydrogen, hydroxy, —O—$C_{1-6}$ alkyl, —OC(O)$R^x$, —OC(O)O$R^x$, —OC(O)NH$R^x$, —OC(O)NR'$_6$R'$_7$, —OCH$_2$OR, —OC($R^x$)$_2$OR, —OCH$R^x$OR, —OCH$_2$OCH$_2$SCH$_3$, OP(O)(OH)$_2$, OCH$_2$OP(O)(OH)$_2$, —OCH$_2$OCH$_2$OP(O)(OH)$_2$, —(OCH$_2$)$_n$OC=OCH$_2$NHR$^x$, —(OCH$_2$)$_n$OC(=O)CH(R")NR'$_6$R'$_7$, where n is 0–3, OCH$_2$SR, —OC($R^x$)$_2$SR, —OCH$R^x$SR, —OCOCH$_2$CH$_2$NH$_3^+$ HCOO$^-$, —OCOCH$_2$CH$_2$COOH, —OCO(CH$_2$)$_3$COOH,—OC(O)(CH$_2$)$_n$NR$^F$R$^G$, where n is 0–3, —OC(O)—Z—C(O)—R', —OC(O)CH$_2$CH$_2$C(O)OCH$_2$CH$_2$OH or when taken together with $R^{19}$ forms a cyclopropane ring;

$R^{19}$ is methyl or when taken together with $R^7$ forms a cyclopropane ring; and $R^{10}$ is hydrogen, hydroxy, —OC(O)$R^x$, —OC(O)O$R^x$, —O—$C_{1-6}$ alkyl, —OCH$_2$OCH$_3$, —OCH$_2$OCH$_2$OCH$_3$, —OCH$_2$OCH$_2$OCH$_2$CH$_3$, —OCH$_2$OCH$_2$CH$_2$OCH$_3$, —OCH$_2$OCH$_2$CH$_2$OH, —OCH$_2$SR, —OCH$_2$OCH$_2$SCH$_3$, —OC(O)NR'$_6$R'$_7$, $C_{1-6}$ alkyl, —(CH$_2$)$_3$C(O)$R^x$, —(CH$_2$)$_3$C(O)O$R^x$, —(CH$_2$)$_3$CN,—OP(O)(OH)$_2$, —OCH$_2$OP(O)(OH)$_2$, —OCH$_2$OCH$_2$OP(O)(OH)$_2$, —(OCH$_2$)$_n$OC=OCH$_2$NHR$^x$, —(OCH$_2$)$_n$OC(=O)CH(R")NR'$_6$R'$_7$, where n is 0–3, —OCOCH$_2$CH$_2$NH$_3^+$ HCOO$^-$, —OCOCH$_2$CH$_2$COOH, —OCO(CH$_2$)$_3$COOH, —OC(O)—Z—C(O)—R', —OC(O)(CH$_2$)$_n$NR$^F$R$^G$ where n is 0–3, or —OC(O)CH$_2$CH$_2$C(O)OCH$_2$CH$_2$O.

The new products that have the general formula I (which include those of formula II) display a significant inhibitory effect with regard to abnormal cell proliferation, and have therapeutic properties that make it possible to treat patients who have pathological conditions associated with an abnormal cell proliferation. The pathological conditions include the abnormal cellular proliferation of malignant or non-malignant cells in various tissues and/or organs, including, non-limitatively, muscle, bone and/or conjunctive tissues; the skin, brain, lungs and sexual organs; the lymphatic and/or renal system; mammary cells and/or blood cells; the liver, digestive system, and pancreas; and the thyroid and/or adrenal glands. These pathological conditions can also include psoriasis; solid tumors; ovarian, breast, brain, prostate, colon, stomach, kidney, and/or testicular cancer, Karposi's sarcoma; cholangiocarcinoma; choriocarcinoma; neuroblastoma; Wilm's tumor, Hodgkin's disease; melanomas; multiple myelomas; chronic lymphocytic leukemias; and acute or chronic granulocytic lymphomas. The novel products in accordance with the invention are particularly useful in the treatment of non-Hodgkin's lymphoma, multiple myeloma, melanoma, and ovarian, urothelial, oesophageal, lung, and breast cancers. The products in accordance with the invention can be utilized to prevent or delay the appearance or reappearance, or to treat these pathological conditions. In addition, the compounds of formula I are useful in treating and/or preventing polycystic kidney diseases (PKD) and rheumatoid arthritis.

The compounds of this invention can be made by techniques from the conventional organic chemistry repertoire. Schemes I–VIII, which depict processes that compounds within the scope of formula I can be made, are only shown for the purpose of illustration and are not to be construed as limiting the processes to make the compounds by any other methods.

The compounds I of this invention are 6-halo or nitrate substituted taxane analogs. All of the contemplated analogs can be prepared from a previously reported 6α,7α-diol intermediate 4 (Scheme I) or suitably substituted analogs. The preparation of this diol intermediate is shown in Scheme I.

As shown in Scheme I, the starting material is a taxane analog suitably protected to leave the most reactive hydroxy group at C-7. Compound 1 in Scheme I is protected at the 2' hydroxy group at the sidechain. The example of compound 1 actually described utilizes a silyl protecting group at the 2'position, but other protecting groups could be utilized. The preparation of intermediate 1 are now well known in the art. The synthesis of diol 4 utilizes precursor 6,7-olefin analog 3 which is also now known in the art. The compound 3 can be formed directly from intermediate 1 upon treatment with a reagent such as DAST as described in the U.S. Pat. No. 5,380,751. The synthesis of olefin 3 described in Scheme I proceeds through the 7-trifluoromethanesulfonate (triflate) intermediate 2 which is prepared as shown in step A. Elimination of the triflate (step B) provides the desired olefins 3. The preparation of 7-O triflate and its conversion into cyclopropane and olefin has been divulged by Johnson, R. A., et al., *Taxol chemistry. 7-O-Triflates as precursors to olefins and cyclopropanes. Tetrahedron Letters,* 1994. 35(43): p. 7893–7896 & by the same authors in WO 94/29288.

The olefin 3 is then hydroxylated with Osmium tetroxide (step C) which is used in either stoichiometric quantities or catalytically in the presence of a cooxidant such as N-methyl morpholine-N oxide (NMO). A patent application on such diol intermediates which includes some methods of its preparation has been published: Roth et. al. 6,7 EP 0 600 517 A1. A protected taxane diol intermediate has also been described in the literature by Liang et. al. *Tetrahedron Letters* 1995, 36(17) 2901–2904. and ibid. 1995, 36(43) 7795–7798. The osmium reagent only reacts from the face of the double bond which is down or a as the taxane core is depicted in this document. Thus this reaction provides only one stereoisomer.

The prefered scheme for preparing 6-halo derivatives is presented in schemes II–VII. The diol 4 is selectively oxidized in step D at the 6-hydroxyl. Many oxidants can be used for this oxidation which include TPAP and a co-oxidant such as N-methyl-morpholine N-oxide, $CrO_3$ in sulfuric acid and water commonly refered to as the Jones reagent, preferably the combination of a catalytic amount of 4-benzoyloxy—TEMPO in the presence of KBr and chlorox® bleach as the co-oxidant. Step E accomplishes the epimerization of the 7-hydroxyl and the reduction of the 6-ketone to afford the cis diol 6. Step E preferably uses silica gel in methlylene chloride to accomplish the epimerization of the 7 hydroxyl group but stirring in dilute acid such as pyridium para-toluene sulfonic acid or placing the material on a silica gel column and eluting with a 1:1 hexane ethyl acetate mixture will also accomplish the desired epimerization. The epimerized hydroxy ketone is then reduced directly with triacetoxyborohydride to afford diol 6. Any number of commerically available borohydrides can be used for this reduction but triacetoxyborohydride gives the best stereoselectivity for this reduction. The resulting diol 6 is then converted to the cyclic sulfate in step F. The cyclic thiocarbonate can also be used to activate the diol to nucleophilic attack at the 6 position. Treatment of the cyclic sulfate in step G (Scheme III) with tetrabutylammonium fluoride gave the corresponding 6-Fluoro taxol (Ia). Other nucleophiles can be substituted for tetrabutylammonium fluoride in step G such as cesium fluoride, potassium fluoride, LiBr in step M (Scheme V), or tetrabutylammonium nitrate (step N, Scheme V).

Derivatives of the 7-hydroxyl can be prepared as illustrated in Schemes III and IV. The most reactive hydroxyl group in compound Ia is protected with a suitable protecting group in step H. The preferable protecting group is the triethylsilyl ether. With the 2' hydroxyl blocked the 7 hydroxyl can be derivatized using methods known in the art. For the purpose of example the 7 hydroxyl is derivatized in step I with chloromethyl methyl ether and the 2' protecting group removed with conditions known to one skilled in the art, preferably 1N HCl in acetonitrile to give compound Ib. Intermediate 8 can also be derivatized using dimethyl sulfide and benzoyl peroxide to give the 7 methylthiomethyl ether 9 as illustrated in Scheme IV, step J. In step K, compound 9 can be deprotected using any conditions known in the art, preferably 1N HCl in acetonitrile to give compound Ic. In step L, preparation of the 7-methyl ether is illustrated. Reducing the methylthiomethyl ether 9 with Nickel boride or preferably Raney nickel in refluxing ethanol followed by deprotection of the 2' protecting group affords the compound of formula Id.

As mentioned above other nucleophiles can be added at the 6 position of the cyclic sulfate. Step M (Scheme V) illustrates the use of LiBr in DMF to introduce a bromide group at the 6 position. Other metal bromides can also be used such as tetrabutylammonium bromide, cesium bromide and potassium bromide. Step N illustrates the addition of the nitrate anion. The preferred reagent is tetrabutylammonium nitrate but other nitrate sources could be used such as lithium nitrate, potassium nitrate and cesium nitrate. The 6-α-nitrate ester can be protected with a suitable protecting group to protect the most reactive hydroxyl as in step O, scheme VI. The triethylsilyl group is the prefered protecting group. Once the 2' hydroxyl is protected the 7-hydroxyl can be derivatized using methods known in the art. Scheme VI, step P illustrates the preparation of methylthiomethyl group followed by deprotection of the triethylsilyl group, preferably with 1N HCl but other organic and inorganic acids can be used. Step Q, in scheme VII illustrates the formation of the 7-methoxymethyl group followed by deprotection of the 2' protecting group using conditions known in the art. Steps P and Q are illustrative of the minipulations at the 7-position which are possible in the presence of the 6-α-nitrate ester.

The 6-β-halides can be prepared from the bromide Ie (see scheme VIII) by first protecting the hydroxyls as in step R using a suitable taxane protecting group such as trialkylsilyl or benzyl carbonate. In step S the α bromide is displaced with a suitable halide source such as tetrabutylammonium, cesium or potassium halide. Deprotection using conditions known in the art provides the β-halide Ij. In a similar manner one could prepare the corresponding 6β-nitrate by using the corresponding nitrate source (i.e. salt) in place of the halide source aforementioned. Alternatively, one could prepare the 6,7 α-epoxide as described in Roth, G. U.S. Pat. No. 5,395,850 (1995) followed by opening with $MgBr_2$ or $MgI_2$ followed by epimerization of the 7-hydroxyl using the method of Kingstonet al., *Modified Taxols*. 10. *Preparation of 7-Deoxytaxol, a Highly Bioactive Taxol Derivative, and Interconversion of Taxol and 7-epi-Taxol. J. Org. Chem.,* 1993 58,: p. 3798–3799.

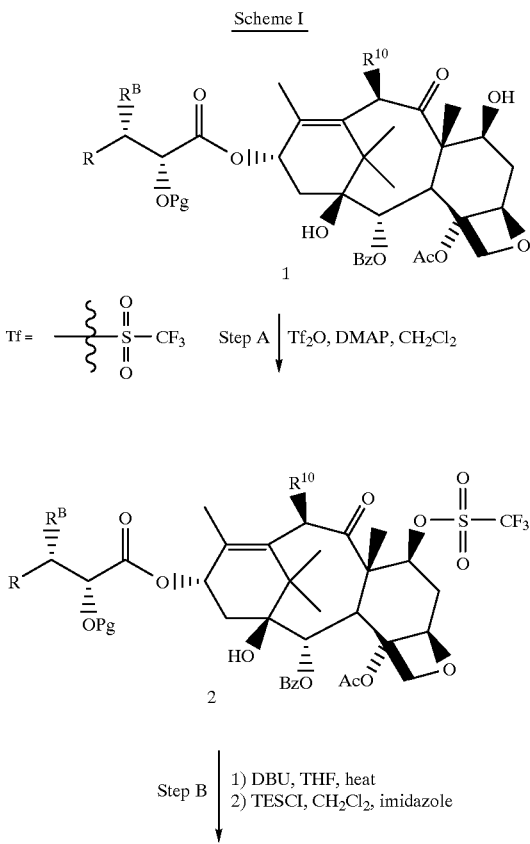

Scheme I

-continued
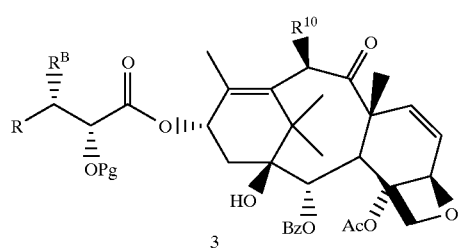
3
Step C | OsO4, NMO,
8:1 Acetone:water
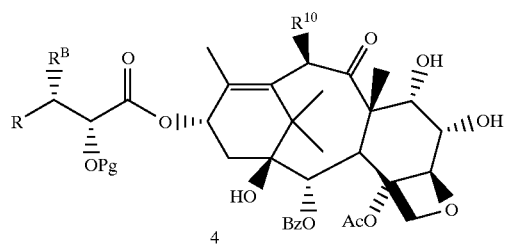
4
Scheme II
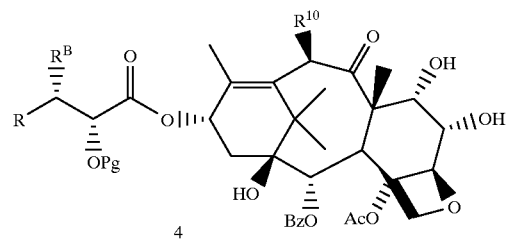
4
step D | 4-BzO-TEMPO, KBr, NaOCl
water, methylene chloride
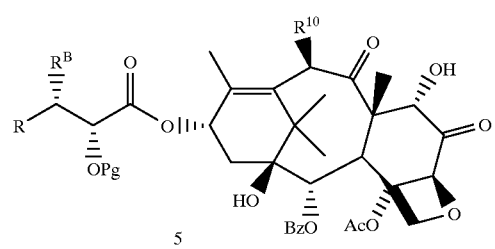
5
step E | silica gel, methylene chloride
Na(OAc)3BH, Acetic acid, acetonitrile, 0° C.
-continued
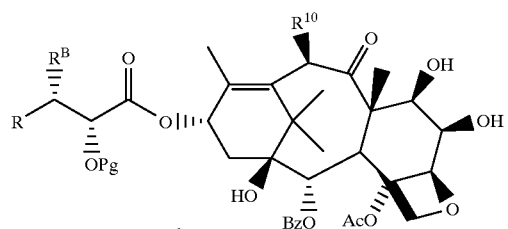
6
step F | thionyl chloride, triethylamine
RuCl3, NaIO4
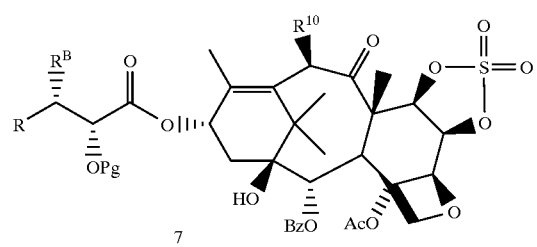
7
Scheme III
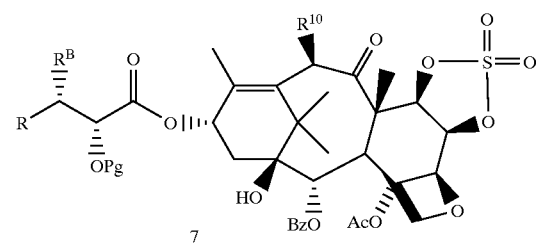
7
step G | tetrabutylammonium fluoride
H2SO4, water, THF
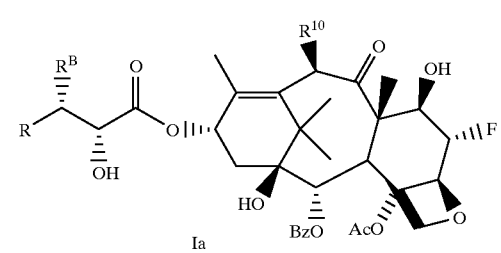
Ia
step H | triethylsilyl chloride
pyridine, methylene chloride -continued
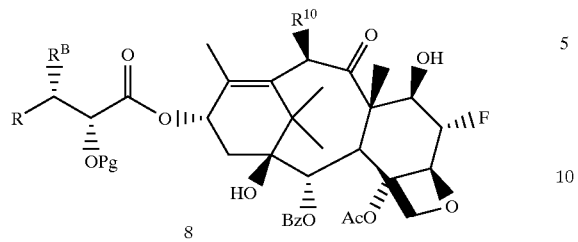
8
step I | chloromethyl methyl ether, diisoproplyethylamine
1N HCl, acetonitrile
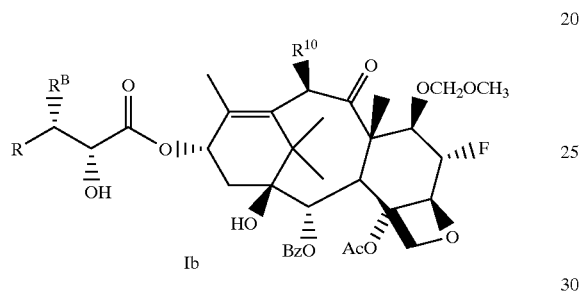
Ib
Scheme IV
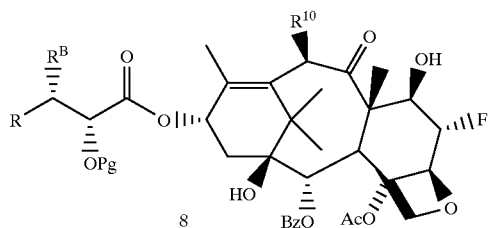
8
step J | Benzoyl peroxide, dimethylsulfide

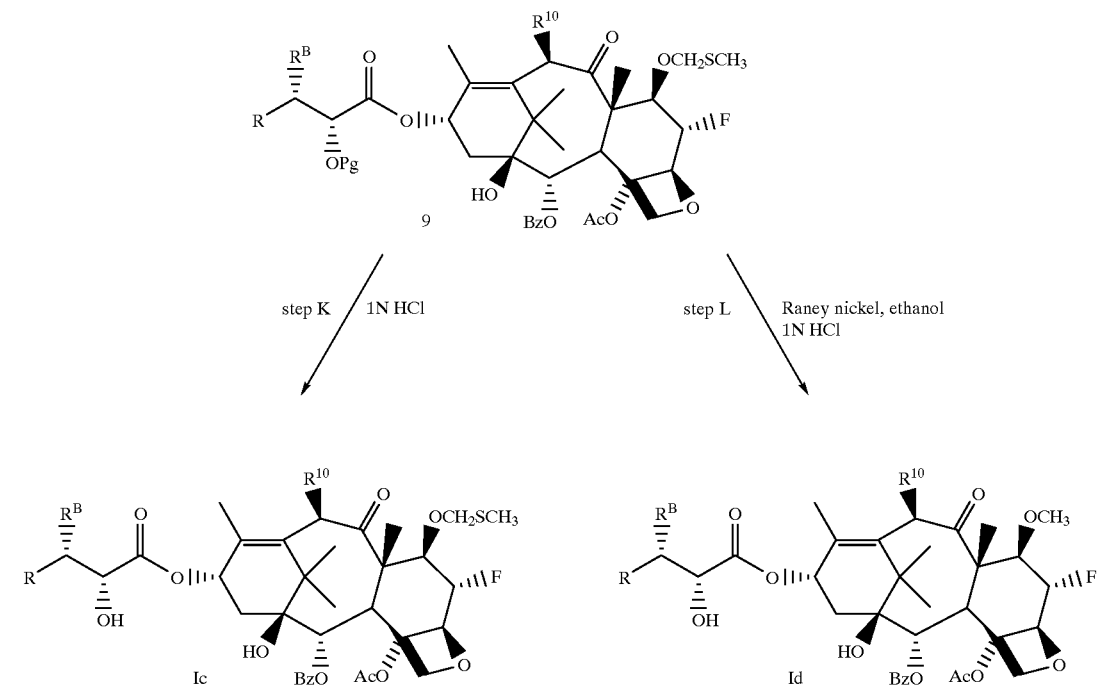
Scheme V
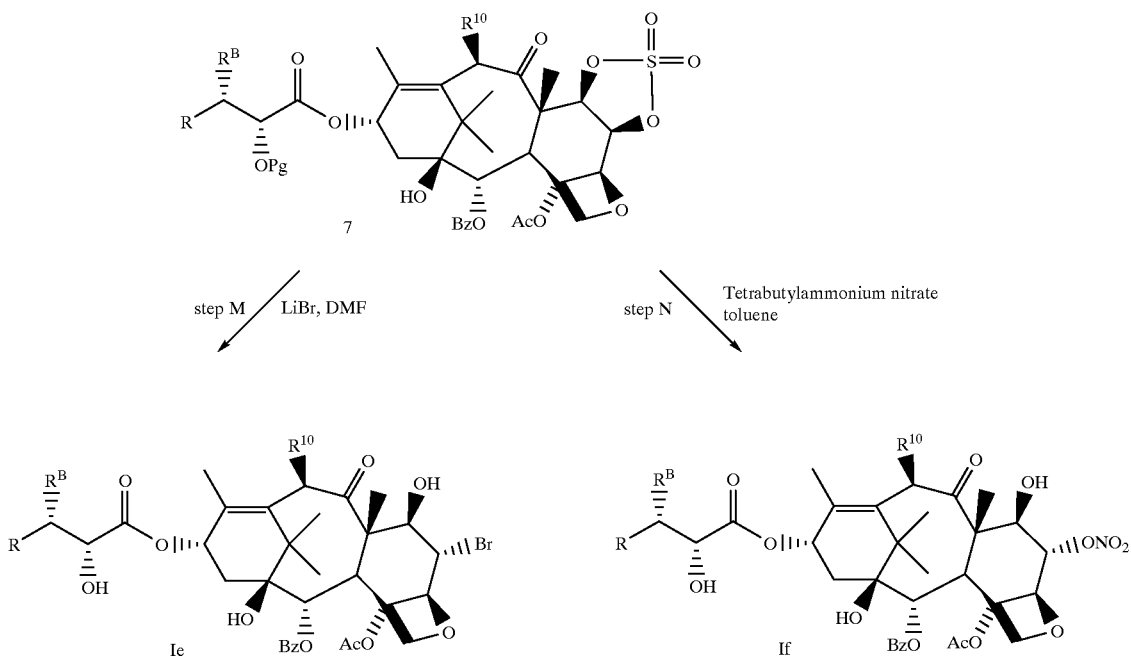

15
Scheme VI
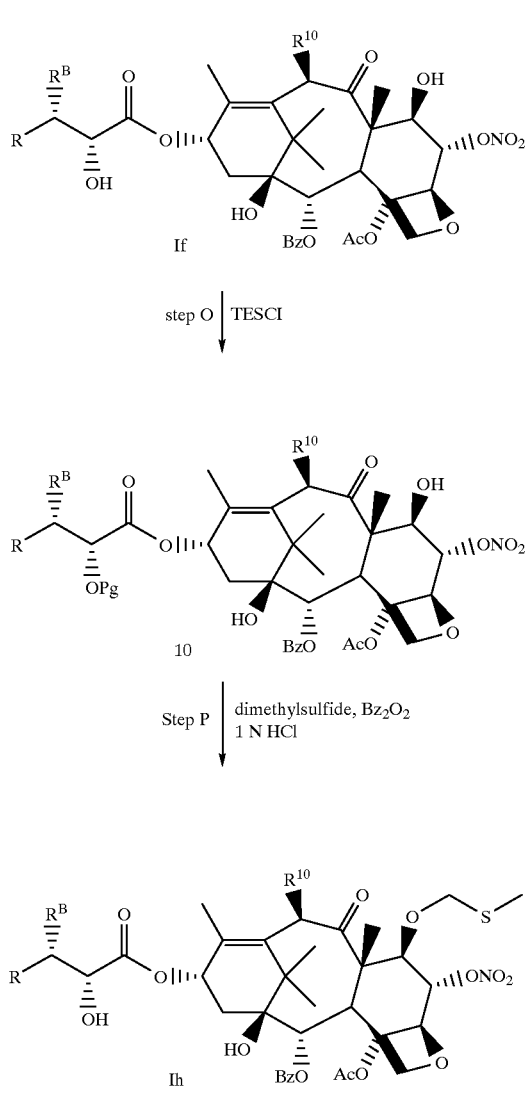
Scheme VII
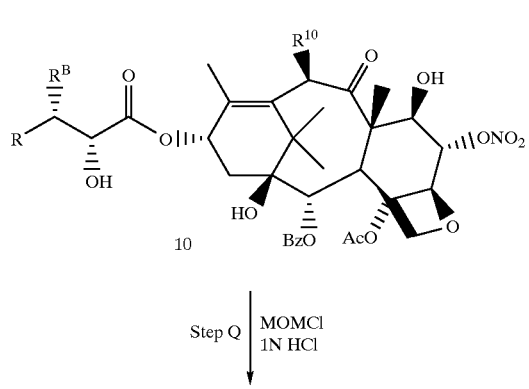
16
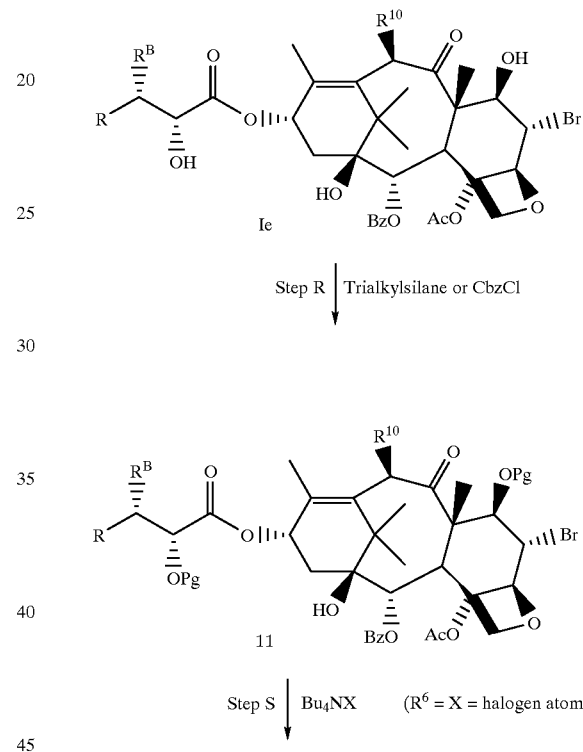

-continued

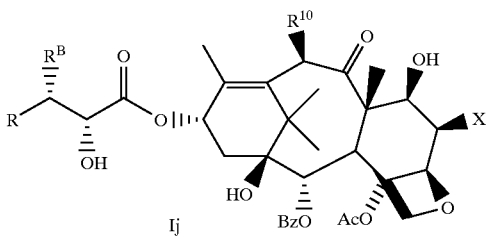

Ij

Some of the schemes refer to a hydroxy protecting group, preferably trialkylsilyl group. It is to be understood that hydroxy protecting group may be a carbonate or ester group —C(O)OR$^x$ or —C(O)R$^x$. Thus when such a group is employed as a hydroxy protecting group, it may either be removed to generate the free hydroxy protecting group or it may remain as a part of the final product.

By now there are many publications teaching the introduction of a wide variety of groups onto a taxane core. By using these well established methods or obvious variants thereof, the starting taxanes of formula I or hydroxy protected analogues thereof, can be readily made. For example, for making C7 unsubstituted (deoxy) derivatives see, European Patent Application 590,267A2 published Apr. 6, 1994 and PCT application WO 93/06093 published Apr. 1, 1993; for making C-10 epi hydroxy or acyloxy compounds see PCT application WO 96/03394; for making C-10 deoxy-C-10 alkyl analogs see PCT application WO95/33740; for making 7β,8β-methano, 6α,7α-dihydroxy and 6,7-olefinic groups see, R. A. Johnson, Tetrahedron Letters, Vol. 35, No 43, pp 7893–7896 (1994), U.S. Pat. No. 5,254,580 issued Oct. 19, 1993, and European Patent Application 600,517A1 published Jun. 8, 1994; for making C7/C6 oxirane see, X. Liang and G. I. Kingston, Tetrahedron Letters, Vol. 36, No. 17, pp 2901–2904 (1995); for making C7-epi-fluoro see, G. Roth et al, Tetrahedron Letters, Vol 36, pp 1609–1612 (1995); for forming C7 esters and carbonates see, U.S. Pat. No. 5,272,171 issued Dec. 21, 1993 and S. H. Chen et al., Tetrahedron, 49, No. 14, pp 2805–2828 (1993); for 9a- and 9b-hydroxy taxanes see, L. L. Klein, Tetrahedron Letters, Vol 34, No 13, pp 2047–2050 (1993), PCT application WO 94/08984 published Apr. 28, 1994, U.S. Pat. No. 5,352,806 issued Oct. 4, 1994, PCT application WO 94/20485 published Sep. 15, 1994, and G. I. Georg et. al. Tetrahedron Letters, Vol 36, No 11, pp 1783–1786 (1995). For making sidechain variations see Robert Holton U.S. Pat. Nos. 5,175, 315 and 5,229,526.

DESCRIPTION OF SPECIFIC EMBODIMENTS

The specific examples that follow illustrate the syntheses of the compounds of the instant invention, and is not to be construed as limiting the invention in sphere or scope. The method may be adapted to variations in order to produce the compound embraced by this invention but not specifically disclosed. Further, variations of the methods to produce the same compound in somewhat different manner will also be evident to one skilled in the art.

In the following experimental procedures, all temperatures are understood to be in Centigrade (C) when not specified. The nuclear magnetic resonance (NMR) spectral characteristics refer to chemical shifts (d) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs or br s), broad doublet (bd or br d), broad triplet (bt or br t), broad quartet (bq or br q), singlet (s), multiplet (m), doublet (d), quartet (q), triplet (t), doublet of doublet (dd), doublet of triplet (dt), and doublet of quartet (dq). The solvents employed for taking NMR spectra are acetone-d$_6$ (deuterated acetone). DMSO-d$_6$ (perdeuterodimethylsulfoxide), D$_2$O (deuterated water), CDCl$_3$ (deuterochloroform) and other conventional deuterated solvents. The infrared (IR) spectral description include only absorption wave numbers (cm$^{-1}$) having functional group identification value.

Celite is a registered trademark of the Johns-Manville Products Corporation for diatomaceous earth.

Silica gel used in the following experimentals is silica gel 60 with a particle size 230–400 mesh obtained from EM Separations Technology.

The abbreviations used herein are conventional abbreviations widely employed in the art. Some of which are: DAB (deacetylbaccatin III); MS (mass spectrometry); HRMS (high resolution mass spectrometry); Ac (acetyl); Ph (phenyl); v/v (volume/volume); FAB (fast atom bombardment); NOBA (m-nitrobenzyl alcohol); min (minute(s)); h or hr(s) (hour(s)); DCC (1,3-dicyclohexylcarbodiimide); BOC (t-butoxycarbonyl); CBZ or Cbz (benzyloxycarbonyl); Bn (benzyl); Bz (benzoyl); Troc (2,2,2-trichloroethyloxycarbonyl), DMS (dimethylsilyl), TBAF (tetrabutylammonium fluoride), DMAP (4-dimethylaminopyridine); TES (triethylsilyl); DMSO (dimethylsulfoxide); THF (tetrahydrofuran); HMDS (hexamethyldisilazane); MeOTf (methyltriflate); NMO (morpholine-N-oxide); (DHQ)$_2$PHAL (hydroquinine 1,4-phthalazinediyl diether). Tf=triflate=trifluoromethanesulfonate; LRMS (low resolution mass spectrometry); ESI (electrospray ionization); TEMPO (2,2,6,6-tetramethyl-1-piperidinyloxy, free radical); DBU (diazobicycloundecene); MOMCl (chloromethyl methyl ether); TPAP (tetrapropyl ammonium peruthenate).

Preparation of Starting Materials (Scheme I)

2'-O-(triethylsilyl)-paclitaxel [1]

Paclitaxel (15 g, 17.57 mmol) was dissolved in a solution of 60 mL of pyridine and 60 mL of dichloromethane and then the mixture was cooled to 0° C. Triethylsilyl chloride (11.8 mL, 70.3 mmol) and the reaction was stirred for 90 min at 0°. The reaction was diluted with ethyl acetate, washed successively with water and then brine, dried over anhydrous magnesium sulfate, filtered, and concentrated in vacuo. The crude material was purified by flash chromatography over silica gel using 2:1 hexane/ethyl acetate as eluent to provide 17.0 g (99%) of the title compound.

2'-O-(triethylsilyl)-7β-O-trifluoromethanesulfonylpaclitaxel [2]

The alcohol 1 (17 g, 17.5 mmol) and DMAP (8.55 g, 70 mmol) was dissolved in dichloromethane and then the mixture was cooled to 0° C. Trifluoromethanesulfonic anhydride (3.39 mL, 20.1 mmol) was added via syringe and then reaction was allowed to warm to ambient temperature. The reaction was stirred for 2 hours, was diluted with ethyl acetate, washed successively with water and then brine, dried over anhydrous magnesium sulfate, filtered, and concentrated in vacuo. The crude material was purified by flash chromatography over silica gel using 2:1 hexane/ethyl acetate as eluent to provide 17.6 g (91%) of the title compound.

2'-O-(triethylsilyl)-6,7-dehydropaclitaxel [3]

The triflate 2 (17.6 g, 16 mmol) was dissolved in 75 mL of dry THF and then 12.18 g (80 mmol) of DBU was added. The reaction was heated at reflux for 2 hours and then diluted with ethyl acetate. The organic layer was washed five times with water and then brine, dried over anhydrous magnesium sulfate, filtered, and concentrated in vacuo. The crude product was dissovled in methylene chloride and then 16 mmol of imidazole and 8 mmol of triethylsilyl chloride were added. The reaction was stirred for 1.5 h at ambient temperature, diluted with ethyl acetate, washed with two portions of water, dried over anhydrous magnesium sulfate and concentrated in vacuo. The crude material was purified by flash chromatography over silica gel using 2:1 hexane/ethyl acetate as eluent to provide 15.0 g (99%) of the title compound.

2'-O-(triethylsilyl)-6α-hydroxy-7-epi-paclitaxel [4]

The olefin 3 was dissolved in 180 mL of acetone and 22.5 mL of water. NMO (4.06 g, 34.74 mmol) and osmium tetraoxide (200 mg, 0.79 mmol) was added and the reaction was stirred for 12 days. Silica gel was added and the reaction was concentrated in vacuo to provide a near free flowing powder which was placed on top of a flash chromatography silica gel column. Elution with 1:1 hexane/ ethyl acetate provided 13.35 g (86%) of the desired diol.

EXAMPLE 1

Preparation of 2'-O-(triethylsilyl)-6-keto-7-epipaclitaxel [5]-(Scheme II)

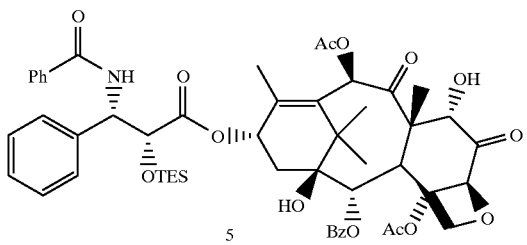

A solution of diol 4 (4.95 g, 5.05 mmol) in 50 mL of dichloromethane at 0° C. was stirred with 4-Benzoyloxy-TEMPO (34 mg, 0.123 mmol) and KBr (61 mg, 0.51 mmol). Then to this solution was added Chlorox® bleach (14.6 mL) which was previously buffered with NaHCO$_3$ (730 mg). The solution was stirred at 0° C. for 1 hour and then diluted with ethyl acetate and washed with 10% sodium thiosulfate solution and then brine. The organic phase was then dried over MgSO$_4$, filtered and concentrated to give 4.94 g of material. An analytical sample was prepared by crystallization from ethyl acetate/hexane to give an amorphous solid.

ESIMS m/z 980 (M−H)

IR (KBr) 3391, 1748, 1714, 1260 cm$^{-1}$ $^1$H NMR (300 MHz, CDCl$_3$) δ 8.15 (d, J=6.9 Hz, 2H), 7.73 (d, J=6.9 Hz, 2H), 7.64–7.30 (m, 11H), 7.09 (d, J=9 Hz, 1H), 6.70 (s, 1H), 6.29 (t, J=9 Hz, 1H), 5.77 (d, J=7.8 Hz, 2H), 5.35 (d, J=12.3 Hz, 1H), 5.02 (s, 1H), 4.71 (d, J=2.1 Hz), 1H), 4.45 (ABq, J=33.3, 8.7 Hz, 2H), 4.16 (d, J=7.5 Hz, 1H), 3.71 (d, J=12.3 Hz, 1H), 2.71 (s, 3H), 2.44 (m, 1H), 2.20 (s, 3H), 2.14 (m, 1H), 1.93 (s, 3H), 1.69 (s, 1H), 1.58 (s, 3H), 1.21 (s, 3H), 1.13 (s, 3H), 0.80 (t, J=8.1 Hz, 9H), 0.43 (m, 6H).

Anal Calcd for C$_{53}$H$_{63}$NO$_{15}$Si: C, 64.81; H, 6.47; N, 1.43. Found: C, 64.88; H, 6.51; N, 1.43.

EXAMPLE 2

Preparation of 2'-O-(triethylsilyl)-6β-hydroxypaclitaxel [6]-(Scheme II)

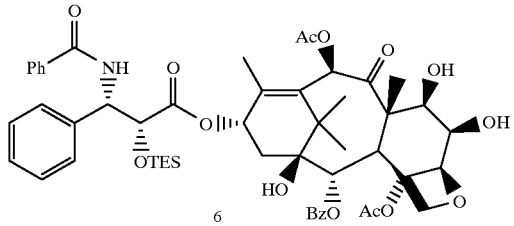

To a solution of the hydroxy ketone 5 (510 mg, 0.52 mmol) in 10 mL of dichloromethane was added an equal wt of silica gel (506 mg) and stirred at ambient temperature for 1 hour. The solution was filtered and the silica gel washed with ethyl acetate several times. The filtrated was concentrated and the residue was dissolved in 5 mL of acetontrile and added to a solution of sodium triacetoxyborohydride prepared by stirring NaBH$_4$ (50 mg, 1.31 mmol) in 2 mL of glacial acetic acid and 5 mL of acetonitrile at 0° C. followed by cooling to −10° C. The solution was stirred for 1 hour at −10° C. and then diluted with ethyl acetate and washed with water, NaHCO$_3$ and brine. The organic fraction was dried over MgSO$_4$, filtered and concentrated. The residue was chromatographed over silica gel using ethyl acetate/hexane (1:1) with 2% methanol to give 384 mg of product (75%).

ESIMS m/z 982 (M−H)

IR (KBr) 3445, 1725, 1241 cm$^{-1}$ $^1$H NMR (300 MHz, CDCl$_3$) δ 8.14 (d, J=6.9 Hz, 2H), 7.73 (d, J=6.9 Hz, 2H), 7.64–7.31 (m, 11H), 7.10 (d, J=9 Hz, 1H), 6.49 (s, 1H), 6.25 (t, J=8.4 Hz, 1H), 5.69 (d, J=7.2 Hz, 2H), 5.07 (d, J=8.7 Hz, 1H), 4.68 (d, J=1.2 Hz, 1H), 4.49 (d, J=8.4 Hz, 1H), 4.27 (m, 1H), 4.21 (d, J=8.4 Hz, 1H), 4.10 (m, 1H), 3.79 (d, J=7.2 Hz, 1H), 3.22 (d, J=9.3 Hz, 1H), 2.64 (d, J=7.5 Hz, 1H), 2.56 (s, 3H), 2.38 (m, 1H), 2.21 (s, 3H), 2.14 (m, 1H), 1.92 (s, 3H), 1.74 (s, 1H), 1.63 (s, 3H), 1.20 (s, 3H), 1.15 (s, 3H), 0.80 (t, J=7.8 Hz, 9H), 0.45 (m, 6H).

Anal Calcd for C$_{53}$H$_{65}$NO$_{15}$Si: C, 64.68; H, 6.66; N, 1.42. Found: C, 64.61; H, 6.64; N, 1.34.

EXAMPLE 3

Preparation of 2'-O-(triethylsilyl)-6,7β-paclitaxelsulfate [7]-(Scheme II)

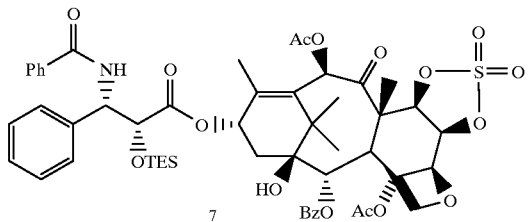

To a solution of the 6,7 β diol 6 (216 mg, 0.220 mmol) in 7 mL of dichloromethane was added triethylamine (120 μL, 0.87 mmol) and the solution cooled to 0° C. At 0° C. thionyl chloride was added (25 μL, 0.336 mmol) and the solution stirred 25 minutes in the cold. The solution was diluted with ethyl acetate and washed with NaHCO$_3$ and brine and dried over MgSO$_4$. The solution was then filtered and concentrated.

The residue was then dissolved in 6 mL of acetonitrile, 6 mL of carbon tetrachoride and 9 mL of water and cooled to 0° C. To this mixture was added NaIO$_4$ (94 mg, 0.439 mmol) and RuCl$_3$ (3.4 mg, 0.016 mmol). After stirring for 30 minutes the solution was diluted with ethyl acetate and washed with water and brine. The solution was dried over MgSO$_4$ and concentrated. The residue was chromatographed over silica gel using hexane/ethyl acetate (2:1) to give 206 mg (89%) of the sulfate.

ESIMS m/z 1046 (M+H)

IR (KBr) 3440, 1753, 1728, 1239, 1214, 980 cm$^{-1}$ $^1$H NMR (300 MHz, CDCl$_3$) δ 8.13 (d, J=7.2 Hz, 2H), 7.73 (d, J=7.2 Hz, 2H), 7.65–7.32 (m, 11H), 7.07 (d, J=9 Hz, 1H), 6.54 (s, 1H), 6.23 (t, J=9.2 Hz, 1H), 5.79 (d, J=6.9 Hz, 1H), 5.70 (d, J=9 Hz, 1H), 5.28 (d, J=7.5 Hz, 1H), 5.12 (d, J=7.2 Hz, 1H), 5.06 (d, J=7.2 Hz, 1H), 4.69 (d, J=1.2 Hz, 1H), 4.50 (d, J=8.1 Hz, 1H), 4.22 (d, J=8.1 Hz, 1H), 3.69 (d, J=6.6 Hz, 1H), 2.58 (s, 3H), 2.30 (m, 1H), 2.21 (s, 3H), 2.16 (m, 1H), 1.98 (s, 3H), 1.93 (s, 1H), 1.75 (s, 3H), 1.21 (s, 3H), 1.16 (s, 3H), 0.8 (t, J=7.8 Hz, 9H), 0.47 (m, 6H).

Anal Calcd for C$_{53}$H$_{63}$NO$_{17}$SSi: C, 60.85; H, 6.07; N, 1.34. Found: C, 60.68; H, 6.12; N, 1.26.

EXAMPLE 4

Preparation of 6α-Fluoropaclitaxel [Ia]-(Scheme III)

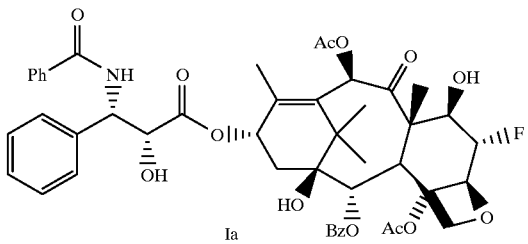

To a solution of the sulfate 7 (30 mg, 0.028 mmol) in 0.5 mL of THF was added tetrabutylammonium fluoride (1.0 M in THF, 70 μL, 0.070 mmol) and stirred for 3 hours until all the starting material was consumed by TLC. Then 9 μL of water and 25 μL of concentrated sulfuric acid was added to the solution and stirred for 1 hour. The solution was diluted with ethyl acetate and washed with saturated bicarbonate solution and brine and dried over MgSO$_4$. The solution was filtered, concentrated and the residue chromatographed over silica gel with hexane/ethyl acetate (1:1) to give 15.7 mg of fluoride (66%).

ESIMS m/z 872 (M+H)

IR (KBr) 3440, 1725, 1243, 1070 cm$^{-1}$ $^1$H NMR (300 MHz, CDCl$_3$) δ 8.12 (d, J=7.2 Hz, 2H), 7.73 (d, J=7.2 Hz, 2H), 7.64–7.32 (m, 11H), 6.96 (d, J=8.7 Hz, 1H), 6.28 (s, 1H), 6.22 (t, J=8.1 Hz, 1H), 5.78 (dd, J=8.9, 2.1 Hz, 1H), 5.65 (d, J=6.0 Hz, 1H), 4.95 (d, J=25.6 Hz, 1H), 4.78 (m, 1.5H), 4.63 (d, J=8.4 Hz, 0.5H), 4.47 (dd, J=17.7, 8.1 Hz, 1H), 4.3 (d, J=9 Hz, 1H), 4.19 (d, J=9 Hz, 1H), 3.96 (d, J=7.2 Hz, 1H), 3.50 (br s, 1H), 2.86 (br s, 1H), 2.41 (s, 3H), 2.31 (m, 2H), 2.23 (s, 3H), 1.81 (s, 3H), 1.70 (br s, 1H), 1.65 (s, 3H), 1.23 (s, 3H), 1.12 (s, 3H).

Anal Calcd for C$_{47}$H$_{50}$FNO$_{14}$: C, 64.74; H, 5.78; N, 1.61. Found: C, 64.73; H, 5.90; N, 1.54.

EXAMPLE 5

Preparation of 2'-O-(triethylsilyl)-6α-Fluoropaclitaxel [8]-(Scheme III)

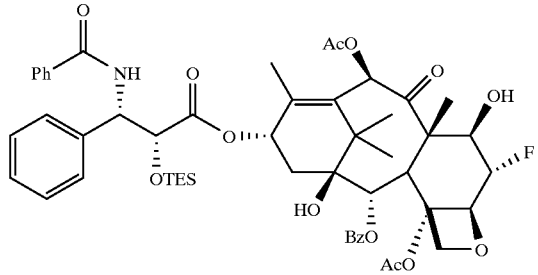

To a solution of the 6α fluoropaclitaxel Ia (400 mg, 0.459 mmol) in 5 mL of pyridine and 5 mL of dichloromethane was added triethylsilylchloride (0.60 mL, 3.6 mmol) at 0° C. The solution was stirred for 30 minutes in the cold and then warmed to ambient temperature for 2 hours. The solution was diluted with ethyl acetate and washed with water and brine and dried over MgSO$_4$. The solution was filtered and concentrated and the residue chromatographed over silica gel with hexane/ethyl acetate (2:1) to give 327 mg of the 2'silyl ether (72%)

ESIMS m/z 984 (M–H)

IR (KBr) 3440, 1727, 1242, 1070 cm$^{-1}$ $^1$H NMR (300 MHz, CDCl$_3$) δ 8.12 (d, J=7.0 Hz, 2H), 7.74 (d, J=7.0 Hz, 2H), 7.63–7.31 (m, 11H), 7.10 (d, J=9 Hz, 1H), 6.30 (s, 1H), 6.27 (t, J=8.4 Hz, 1H), 5.70 (d, J=10.8 Hz, 1H), 5.67 (d, J=7.2 Hz, 1H), 5.00 (d, J=25.8 Hz, 1H), 4.73 (ABq, J=36.9, 8.4 Hz, 1H), 4.68 (d, J=2.1 Hz, 1H), 4.50 (m, 1H), 4.27 (ABq J=36.9, 8.4 Hz, 2H), 3.99 (d, J=6.6 Hz, 1H), 2.81 (d, J=3.9 Hz, 1H), 2.56 (s, 3H), 2.40 (m, 1H), 2.23 (s, 3H), 2.16 (m, 1H), 1.93 (s, 3H), 1.69 (s, 1H), 1.66 (s, 3H), 1.24 (s, 3H), 1.12 (s, 3H), 0.80 (t, J=8.1 Hz, 9H), 0.43 (m, 6H).

Anal Calcd for C$_{53}$H$_{64}$FNO$_{14}$Si: C, 64.55; H, 6.54; N, 1.42. Found: C, 64.41; H, 6.36; N, 1.21.

EXAMPLE 6

Preparation of 7-O-Methoxymethyl-6α-Fluoropaclitaxel [Ib]-(Scheme III)

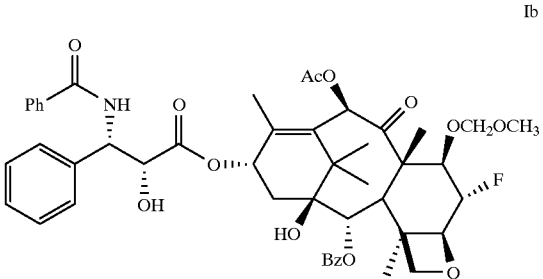

To a solution of the 2'-O-triethylsilyl-6α-Fluoropaclitaxel 8 (327 mg, 0.332 mmol) in 10 mL of dichloromethane was added diisopropylethylamine (1.2 mL, 6.88 mmol) and chloromethyl methyl ether (0.50 mL, 6.88 mmol). The solution was stirred 72 hours and diluted with ethyl acetate and washed with water and brine. The solution was dried over MgSO$_4$, filtered and concentrated. The residue was dissolved in 5 mL of acetonitrile and cooled to 0° C. The solution was then treated with 1N HCl (45 μL, 0.045 mmol) and stirred for 1 hour. The solution was diluted with ethyl acetate and washed with saturated bicarbonate solution and then brine. The organic fraction was then dried over MgSO$_4$, filtered and concentrated. The residue was chromatographed over silica gel with hexane/ ethyl acetate (1:1) to give 254 mg of product (83%).

ESIMS m/z 914 (M−H)

IR (KBr) 3417, 1720, 1240, 1115 cm$^{-1}$ $^1$H NMR (300 MHz, CDCl$_3$) δ 8.10 (d, J=6.9 Hz, 2H), 7.75 (d, J=6.9 Hz, 2H), 7.64–7.34 (m, 11H), 7.02 (d, J=9 Hz, 1H), 6.52 (s, 1H), 6.19 (t, J=7.8 Hz, 1H), 5.80 (d, J=8.7 Hz, 1H), 5.66 (d, J=6.0 Hz, 1H), 4.94 (d, J=6.6 Hz, 1H), 4.32–4.16 (m, 3H), 4.00 (d, J+6.9 Hz, 1H), 3.52 (br s, 1H), 3.28 (s, 3H), 2.40 (s, 3H), 2.32 (d, J=8.7 Hz, 2H), 2.18 (s, 3H), 1.94 (s, 3H), 1.70 (s, 4H), 1.20 (s, 3H), 1.17 (s, 3H).

Anal Calcd for C$_{49}$H$_{54}$FNO$_{15}$: C, 64.25; H, 5.94; N, 1.53. Found: C, 64.03; H, 5.83; N, 1.50.

EXAMPLE 7

Preparation of 2'-O-(triethylsilyl)-7-O-Meththiomethyl-6α-Fluoropaclitaxel [9]-(Scheme IV)

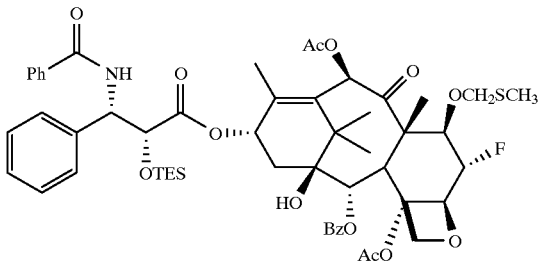

9

To a solution of the 2'-O-triethylsilyl-6α-Fluoropaclitaxel 8 (988 mg, 1.003 mmol) in 20 mL of acetonitrile was added dimethylsulfide (0.737 mL, 10.03 mmol) and cooled to 0° C. To this solution was added benzoyl peroxide (1.21 g, 5.015 mmol) and the solution stirred for 30 minutes and then warmed to ambient temperature for 30 minutes. The solution was diluted with ethyl acetate and washed with saturated bicarbonate solution, water and brine. The organic fraction was dried over MgSO$_4$, filtered and concentrated. The residue was chromatographed over silica gel with hexane/ ethyl acetate (3:1 then 1:1) to give 859 mg of product (82%).

ESIMS m/z 1044 (M−H)

IR (KBr) 3441, 1727, 1268, 1230, 1068, 993 cm$^{-1}$ $^1$H NMR (300 MHz, CDCl$_3$) δ 8.12 (d, J=7.2 Hz, 2H), 7.74 (d, J=7.2 Hz, 2H), 7.61–7.31 (m, 11H), 7.10 (d, J=9 Hz, 1H), 6.70 (s, 1H), 6.25 (t, J=9.3 Hz, 1H), 5.68 (m, 2H), 5.05–4.84 (m, 4H), 4.71 (d, J=2.1 Hz, 1H), 4.45 (ABq, J=16.2, 7.5 Hz, 1H), 4.34 (d, J=8.4 Hz, 1H), 4.20 (d, J=8.4 Hz, 1H), 4.06 (d, J=6.9 Hz, 1H), 2.58 (s, 3H), 2.40 (s, 1H), 2.20 (m, 1H), 2.19 (s, 3H), 2.13 (s, 6H), 1.70 (s, 4H), 1.18 (s, 6H), 0.82 (t, J=8.4 Hz, 9H), 0.47 (m, 6H).

Anal Calcd for C$_{55}$H$_{68}$FNO$_{14}$SSi: C, 63.14; H, 6.55; N, 1.34. Found: C, 63.03; H, 6.42; N, 1.18.

EXAMPLE 8

Preparation of 7-O-Meththiomethyl-6α-Fluoropaclitaxel [Ic]-(Scheme IV)

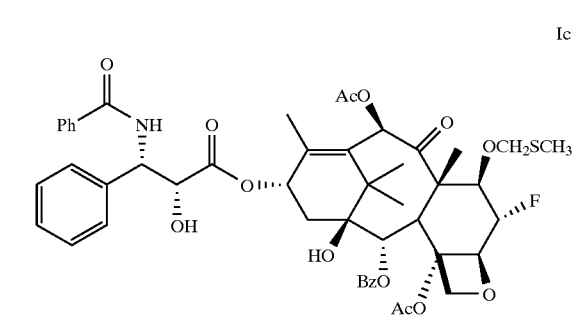

Ic

To a solution of the silyl ether 9 (404 mg, 0.387 mmol) in 10 mL of acetonitrile at 0° C. was added 1N HCl (0.773 mL, 0.773 mmol) and the solution stirred for 1 hour. The solution was diluted with ethyl acetate and washed with saturated bicarbonate solution, water and brine. The organic fraction was dried over MgSO$_4$, filtered and concentrated. The residue was chromatographed over silica gel with hexane/ ethyl acetate (1.5:1) to give 287 mg of a white amorphous solid after crystallization from ethyl acetate and hexane (79%).

ESIMS m/z 932 (M+H)

IR (KBr) 3440, 1726, 1267, 1230, 1068, 992 cm$^{-1}$ $^1$H NMR (300 MHz, CDCl$_3$) δ 8.06 (d, J=7.5 Hz, 2H), 7.72 (d, J=7.5 Hz, 2H), 7.61–7.32 (m, 11H), 7.01 (d, J=9 Hz, 1H), 6.68 (s, 1H), 6.23 (t, J=8.4 Hz, 1H), 5.83 (d, J=8.4 Hz, 1H), 5.67 (d, J=6.9 Hz, 1H), 5.05–4.83 (m, 5H), 4.45 (ABq, J=16.5, 7.8 Hz, 1H), 4.33 (d, J=8.1 Hz, 1H), 4.19 (d, J=8.1 Hz, 1H), 4.04 (d, J=6.6 Hz, 1H), 3.52 (br s, 1H), 2.44 (s, 3H), 2.35 (d, J=9 Hz, 2H), 2.19 (s, 3H), 2.14 (s, 3H), 2.03 (s,3H), 1.69 (m, 1H), 1.58 (s, 3H), 1.21 (s, 6H).

Anal Calcd for C$_{49}$H$_{54}$FNO$_{14}$S C, 63.15; H, 5.84; N, 1.50. Found: C, 62.98; H, 5.82; N, 1.46.

EXAMPLE 9

Preparation of 7-O-Methyl-6α-Fluoropaclitaxel [Id]-(Scheme IV)

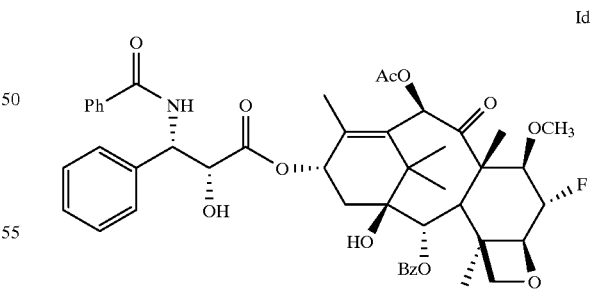

Id

To a solution of the 2'-O-triethylsilyl-7-O-methylthiomethyl ether 9 (445 mg, 0.426 mmol) was added excess Raney Nickel (washed with water until the washings were pH neutral) in 20 mL of absolute ethanol. The solution was refluxed for 1.5 hours and cooled. The solution was filtered through a pad of Celite and concentrated. The residue was dissolved in 20 mL of acetonitrile and cooled to 0° C. and 1N HCl added (0.852 mL, 0.852 mmol) and the solution stirred for 1 hour. The solution was diluted with ethyl acetate and washed with saturated bicarbonate solution, water and brine. The organic fraction was dried over MgSO$_4$, filtered and concentrated. The residue was chromatographed over silica gel with hexane/ ethyl acetate (1.5:1) and then rechromatographed with methylene chloride / acetonitrile / methanol (84:15:1) to give 224 mg of product (59%).

ESIMS m/z 886 (M+H)

IR (KBr) 3415, 1714, 1240, 1117 cm$^{-1}$ $^1$H NMR (300 MHz, CDCl$_3$) δ 8.09 (d, J=7.2 Hz, 2H), 7.76 (d, J=7.2 Hz, 2H), 7.61–7.34 (m, 11H), 7.03 (d, J=9 Hz, 1H), 6.39 (s, 1H), 6.19 (br t, 1H), 5.80 (d, J=9 Hz, 1H), 5.63 (d, J=6.9 Hz, 1H), 4.97–4.76 (m, 3H), 4.29 (d, J=8.4 Hz, 1H), 4.15 (d, J=8.4 Hz, 1H), 3.99–3.88 (m, 2H), 3.55 (s, 3H), 3.52 (d, J=5.1 Hz, 1H), 2.40 (s, 3H), 2.32 (m, 2H), 2.21 (s, 3H), 1.86 (s, 3H), 1.70 (s, 1H), 1.65 (s, 3H), 1.21 (s, 3H), 1.18 (s, 3H).

Anal Calcd for C$_{48}$H$_{52}$FNO$_{14}$: C, 65.08; H, 5.92; N, 1.58. Found: C, 64.85; H, 5.85; N, 1.57.

EXAMPLE 10

Preparation of 6α-Bromopaclitaxel [Ie]-(Scheme V)

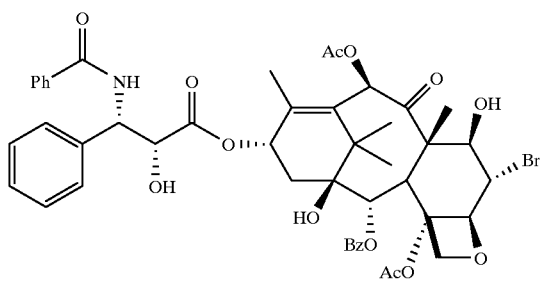

To a solution of the cyclic sulfate 7 (111 mg, 0.106) in 5 mL of DMF was added LiBr (92 mg, 1.06 mmol) and the solution heated to 70° C. for 15 hours. The solution was diluted with ethyl acetate and washed with water and brine and dried over MgSO$_4$. The organic fraction was filtered and concentrated and the residue chromatographed over silica gel using hexane/ ethyl acetate (1:1) to give 74 mg of the bromohydrin (75%).

ESIMS m/z 932 (M+H)

IR (KBr) 3441, 1725, 1240, 1071 cm$^{-1}$ $^1$H NMR (300 MHz, CDCl$_3$) δ 8.11 (d, J=7.2 Hz, 2H), 7.74 (d, J=7.2 Hz, 2H), 7.65–7.32 (m, 11H), 6.95 (d, J=9 Hz, 1H), 6.29 (s, 1H), 6.24 (t, J=9.3 Hz, 1H), 5.79 (dd, J=9, 2.1 Hz, 1H), 5.65 (d, J=6.9 Hz, 1H), 5.23 (s, 1H), 4.80 (m, 1H), 4.45 (dd, J=9.6, 3.6 Hz, 1H), 4.20 (m, 3H), 3.98 (d, J=7.2 Hz, 1H), 3.46 (d, J=5.1 Hz, 1H), 2.91 (d, J=3.9 Hz, 1H), 2.44 (s, 3H), 2.33 (m, 2H), 2.23 (s, 3H), 1.84 (s, 3H), 1.72 (s, 1H), 1.67 (s, 3H), 1.23 (s, 3H), 1.14 (s, 3H).

Anal. Calcd for C$_{47}$H$_{50}$BrNO$_{14}$: C, 60.52; H, 5.40; N, 1.50. Found: C, 60.25; H, 5.58; N, 1.35.

EXAMPLE 11

Preparation of paclitaxel-6α-nitrate [If]-(Scheme V)

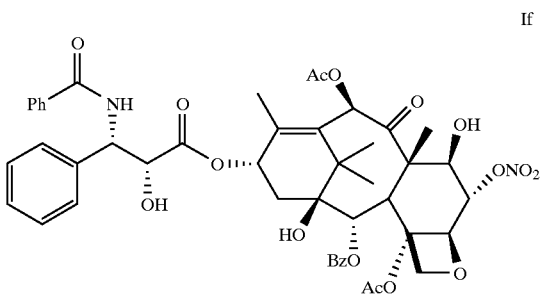

To a solution of the cyclic sulfate 7 (1.64 g, 1.57 mmol) in 30 mL of toluene was added tetrabutylammonium nitrate (950 mg, 3.12 mmol) and the solution heated at 100° C. for 15 hours. The solution was cooled and concentrated. The residue was dissolved in 15 mL of anhydrous THF and stirred with 56 μL of water and 156 μL of concentrated sulfuric acid for 9 hours. Solid NaHCO$_3$ was added (600 mg) and the reaction stirred 15 minutes and then filtered through a pad of Celite and the Celite rinsed several times with ethyl acetate. The filtrate was concentrated and the residue chromatographed over silica gel using hexane/ ethyl acetate (1:1) to give 1.092 grams of the nitrate ester (76%).

ESIMS m/z 915 (M+H)

IR (KBr) 3440, 1726, 1644, 1283, 1241, 1070 cm$^{-1}$ $^1$H NMR (300 MHz, CDCl$_3$) δ 8.08 (d, J=7.2 Hz, 2H), 7.71 (d, J=7.2 Hz, 2H), 7.63–7.31 (m, 11H), 7.07 (d, J=9 Hz, 1H), 6.22 (s, 1H), 6.18 (t, J=8.7 Hz, 1H), 5.73 (dd, J=8.7, 2.4 Hz, 1H), 5.63 (d, J=7.2 Hz, 1H), 5.15 (s, J=9.3 Hz, 1H), 4.80 (s, 1H), 4.76 (d, J=2.4 Hz, 1H), 4.40 (s, J=9 Hz, 1H), 4.24 (ABq, J=20.1, 8.4 Hz, 2H), 3.88 (d, J=6.9 Hz, 1H), 3.70 (br s, 1H), 3.25 (br s, 1H), 2.37 (s, 3H), 2.30 (d, J=7.2 Hz, 2H), 2.23 (s, 3H), 2.02 (s, 1H), 1.80 (s, 3H), 1.77 (s, 3H), 1.20 (s, 3H), 1.10 (s, 3H).

EXAMPLE 12

Preparation of 2'-O-triethylsilyl paclitaxel-6α-nitrate [10]-(Scheme VI)

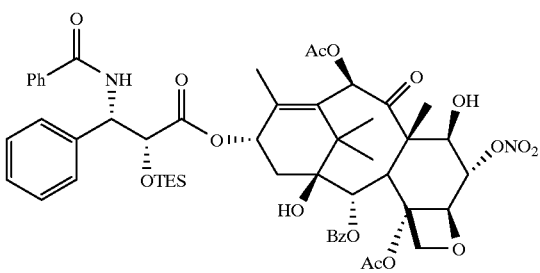

To a solution of the 6-α-nitrate (460 mg, 0.504 mmol) in 7 mL of pyridine and 7 mL of methylene chloride was added DMAP (16 mg, 0.131 mmol) and TESCl (0.42 mL, 2.52 mmol). The solution was stirred for 3 hours and diluted with ethyl acetate. The solution was washed with water (3×) and brine and dried over MgSO$_4$. The solution was filtered, concentrated and the residue chromatographed over silica gel using hexane/ethyl acetate (1.5:1) to give 454 mg of silyl ether 10 (87%).

ESIMS m/z 1029 (M+H)

IR (KBr) 3441, 2361, 1727, 1642, 1283, 1241, 1070 cm$^{-1}$ $^1$H NMR (300 MHz, CDCl$_3$) δ 8.12 (d, J=7.2 Hz, 2H), 7.73 (d, J=7.2 Hz, 2H), 7.64–7.29 (m, 11H), 7.09 (d, J=9 Hz, 1H), 6.26 (t, J=7.5 Hz, 1H), 6.24 (s, 1H), 5.20 (d, J=9.3 Hz, 1H), 4.85 (s, 1H), 4.67 (d, J=1.8 Hz, 1H), 4.46 (dd, J=9,4.2 Hz, 1H), 4.34 (d, J=8.4 Hz, 1H), 4.28 (d, J=8.4 Hz, 1H), 3.93 (d, J=6.9 Hz, 1H), 2.87 (d, J=4.2 Hz, 1H), 2.55 (s, 3H), 2.38 (m, 1H), 2.22 (s, 3H), 2.17 (m, 1H), 1.91 (s, 3H), 1.75 (s, 4H), 1.24 (s, 3H), 1.11 (s, 3H), 0.80 (t, J=7.2 Hz, 9H), 0.43 (m, 6H).

Anal Calcd for C$_{53}$H$_{64}$N$_2$O$_{17}$Si: C, 61.85; H, 6.27; N, 2.72. Found: C, 61.59; H, 6.34; N, 2.50.

EXAMPLE 13

Preparation of 7-O-Methylthiomethylpaclitaxel-6α-nitrate [Ih]-(Scheme VI)

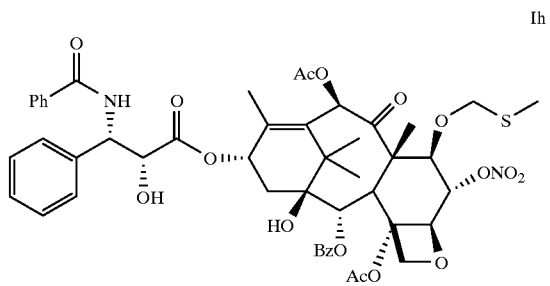

To a solution of the 2'-O-TES-nitrate (195 mg, 0.19 mmol) in 8 mL of acetonitrile at 0° C. was added dimethylsulfide (140 μL, 1.89 mmol) and Benzoyl peroxide (230 mg, 0.95 mmol). The solution was stirred for 20 minutes and then at ambient temperature for 45 minutes. The solution was diluted with ethyl acetate and washed with saturated NaHCO$_3$ and brine and dried over MgSO$_4$. The solution was filtered and concentrated and the residue chromatographed over silica gel using hexane/ethyl acetate (2:1) to give 185 mg of product.

The product was dissolved in 15 mL of acetonitrile and cooled to 0° C. and 68 μL of 1N HCl added. The solution was stirred for 1 hour and diluted with ethyl acetate and washed with saturated NaHCO$_3$ and brine. The solution was dried over MgSO$_4$ and filtered and concentrated. The residue was chromatographed over silica gel using hexane/ethyl acetate (1.5:1) to give 153.6 mg (83% overall) of product.

ESIMS m/z 973 (M–H)

IR (KBr) 3440, 1727, 1645, 1283, 1242, 1068 cm$^{-1}$ $^1$H NMR (300 MHz, CDCl$_3$) δ 8.10 (d, J=7.2 Hz, 2H), 7.75 (d, J=7.2 Hz, 2H), 7.64–7.33 (m, 11H), 6.99 (d, J=9 Hz, 1H), 6.58 (s, 1H), 6.20 (t, J=8.1 Hz, 1H), 5.79 (d, J=8.7 Hz, 1H), 5.66 (d, J=6.9 Hz, 1H), 5.30 (d, J=8.7 Hz, 1H), 4.94–4.72 (m, 4H), 4.32–4.20 (m, 3H), 3.95 (d, J=7.2 Hz, 1H), 3.52 (br s, 1H), 2.40 (s, 3H), 2.32 (d, J=9 Hz, 2H), 2.19 (s, 3H), 2.13 (s, 3H), 1.94 (s, 3H), 1.79 (s, 3H), 1.72 (s, 1H), 1.19 (s, 6H).

Anal Calcd for C$_{49}$H$_{54}$N$_2$O$_{17}$S: C, 60.36; H, 5.58; N, 2.87. Found: C, 60.43; H, 5.44; N, 2.69.

EXAMPLE 14

Preparation of 7-O-Methoxymethylpaclitaxel-6α-nitrate [Ii]-(Scheme VII)

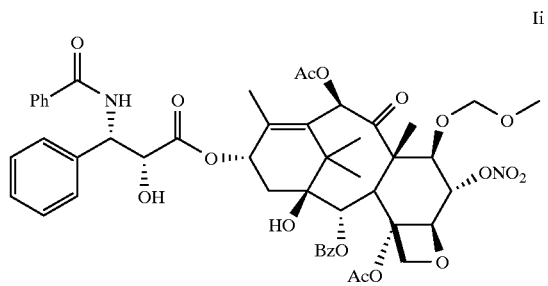

To a solution of the nitrate If (222 mg, 0.216 mmol) in 5 mL of methylene chloride was added diisopropylethyl amine (1.1 mL, 6.31 mmol) and MOMCl (0.310 mL, 4.26 mmol) and the solution stirred for 16 days. The solution was diluted with ethyl acetate and washed with water and brine and dried over MgSO$_4$. The solution was filtered and concentrated and the residue dissolved in 10 mL of acetonitrile and cooled to 0° C. The solution was treated with 1N HCl (0.40 mL, 0.40 mmol) for 30 minutes and diluted with ethyl acetate and washed with saturated NaHCO$_3$ and brine and dried over MgSO$_4$. The solution was filtered and concentrated and the residue chromatographed over silica gel using hexane / ethyl acetate (1:1) to give 189 mg of product (91%).

ESIMS m/z 959 (M+H)

IR (KBr) 3440, 1728, 1645, 1283, 1243, 1106 cm$^{-1}$ $^1$H NMR (300 MHz, CDCl$_3$) δ 8.10 (d, J=7.2 Hz, 2H), 7.76 (d, J=7.2 Hz, 2H), 7.65–7.32 (m, 11H), 7.01 (d, J=9 Hz, 1H), 6.41 (s, 1H), 6.19 (t, J=8.1 Hz, 1H), 5.80 (d, J=9 Hz, 1H), 5.67 (d, J=6.9 Hz, 1H), 5.30 (d, J=8.4 Hz, 1H), 4.80 (m, 2H), 4.70 (ABq, J=12, 7.2 Hz, 2H), 4.32 (d, J=8.4 Hz, 1H), 4.24 (d, J=8.4 Hz, 1H), 4.11 (d, J=7.2 Hz, 1H), 3.94 (d, J=6.9 Hz, 1H), 3.52 (br d, J=4.8 Hz, 1H), 3.25 (s, 3H), 2.43 (s, 3H), 2.31 (m, 2H), 2.19 (s, 3H), 1.88 (s, 3H), 1.82 (s, 3H), 1.73 (br s, 1H), 1.20 (s, 6H).

Anal Calcd for C$_{49}$H$_{54}$N$_2$O$_{18}$: C, 61.37; H, 5.68; N, 2.92. Found: C, 61.35; H, 5.56; N, 2.67.

EXAMPLE 15

Preparation of 6-α-Chloropaclitaxel [Ij]-(Scheme V)

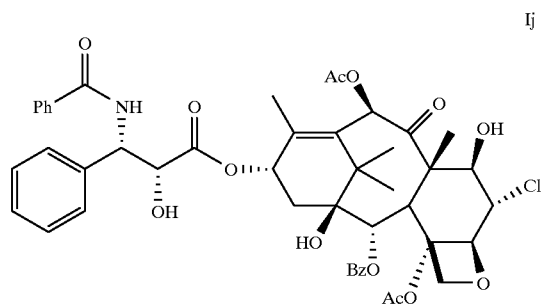

To a solution of the cyclic sulfate 7 (705 mg, 0.675 mmol) in 20 mL of anhydrous DMF was added LiCl (286 mg, 6.75 mmol) and the solution heated to 80° C. for 4 hours. The solution was cooled, diluted with ethyl acetate and washed with water and brine, dried over MgSO$_4$ and concentrated. The residue was dissolved in 10 mL of THF and stirred for 15 minutes with 9 μL of water and 25 μL of concentrated sulfuric acid. The solution was diluted with ethyl acetate and washed with saturated NaHCO$_3$ and brine, dried over MgSO$_4$ and concentrated. The residue was chromatographed over silica gel using hexane/ ethyl acetate (1.5:1) to give 483 mg of the 2-O-TES ether (71%).

ESIMS m/z 1002 (M+H)

IR (KBr) 3442, 1728, 1241, 1070, 981, 710 cm$^{-1}$ $^1$H NMR (300 MHz, CDCl$_3$) δ 8.12 (d, J=7.2 Hz, 2H), 7.77 (d, J=7.2 Hz, 2H), 7.63–7.29 (m, 11H), 7.10 (d, J=9 Hz, 1H), 6.32 (s, 1H), 6.27 (t, J=8.4 Hz, 1H), 5.72 (d, J=9 Hz, 1H), 5.67 (d, J=7.2 Hz, 1H), 5.09 (s, 1H), 4.67 (d, J=2.0 Hz, 1H), 4.43 (dd, J=9.6, 3.6 Hz, 1H), 4.32 (d, J=6.9 Hz, 1H), 2.88 (d, J=3.6 Hz, 1H), 2.59 (s, 3H), 2.43–2.35 (m, 1H), 2.22 (s, 3H), 2.15 (m, 1H), 1.95 (s, 3H), 1.68 (s, 4H), 1.24 (s, 3H), 1.13 (s, 3H), 0.81 (t, J=7.8 Hz, 9H), 0.42 (m, 6H).

Anal Calcd for C$_{53}$H$_{64}$ClNO$_{14}$Si: C, 63.49; H, 6.43; N, 1.40. Found: C, 62.00; H, 6.39; N, 1.28.

To a solution of the 2'-O-TES silyl ether (231 mg, 0.23 mmol) in 10 mL of acetonitrile at 0° C. was added 0.46 mL of 1N HCl and stirred for 1 hour. The solution was diluted with ethyl acetate and washed with saturated NaHCO$_3$ and brine, dried over MgSO$_4$ and concentrated. The residue was chromatographed over silica gel using hexane/ ethyl acetate (1:1) and then crystalized from ethyl acetate/hexane to give 244 mg of amorphous white powder (quant.) of Ij.

ESIMS m/z 888 (M+H)

IR (KBr) 3440, 1725, 1241, 1071 cm$^{-1}$ $^1$H NMR (300 MHz, CDCl$_3$) δ 8.11 (d, J=7.2 Hz, 2H), 7.73 (d, J=7.2 Hz, 2H), 7.64–7.32 (m, 11H), 6.95 (d, J=9 Hz, 1H), 6.29 (s, 1H), 6.23 (t, J=9 Hz, 1H), 5.78 (dd, J=8.8, 2.4 Hz, 1H), 5.65 (d, J=7.2 Hz, 1H), 5.05 (s, 1H), 4.79 (m, 1H), 4.37 (dd, J=9.6, 1.5 Hz, 1H), 4.29 (d, J=8.4 Hz, 1H), 3.45 (d, J=5.4 Hz, 1H), 2.88 (d, J=3.6 Hz, 1H), 2.42 (s, 3H), 2.32 (dd, J=9, 4.2 Hz, 2H), 2.22 (s, 3H), 1.83 (s, 3H), 1.70 (s, 1H), 1.68 (s, 3H), 1.23 (s, 3H), 1.34 (s, 3H).

Anal Calcd for C$_{47}$H$_{50}$ClNO$_{14}$: C, 63.55; H, 5.67; N, 1.58. Found: C, 63.17; H, 5.94; N, 1.52.

EXAMPLE 16

Preparation of 6,7β-Baccatinsulfate [13].

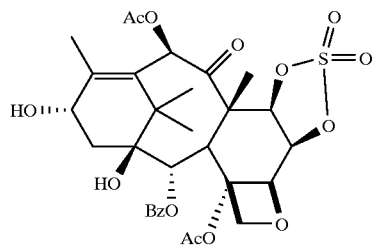

To a solution of the 2'-O-silyl cyclic sulfate 7 (485 mg, 0.464 mmol) in 15 mL of THF was added tetrabutylammonium fluoride (0.511 mL, 0.511 mmol). The reaction was stirred for 15 minutes and then poured into ethyl acetate. The solution was washed with water and brine and then dried over MgSO$_4$. The solution was filtered and concentrated and the residue chromatographed over silica gel using hexane / ethyl acetate (1:1) to give 380 mg of 2'-hydroxy cyclic sulfate (88%).

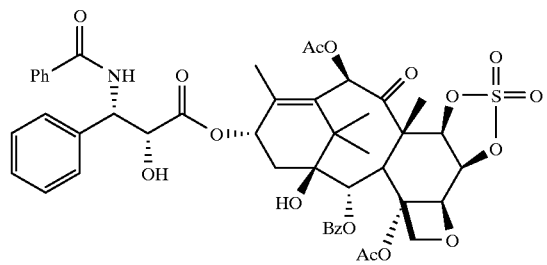

ESIMS m/z 932 (M+H)

IR (KBr) 3431, 1727, 1400, 1239, 1212, 978 cm$^{-1}$ $^1$H NMR (300 MHz, CDCl$_3$) δ 8.12 (d, J=7.2 Hz, 2H), 7.73 (d, J=7.2 Hz, 2H), 7.66–7.33 (m, 11H), 6.93 (d, J=8.7 Hz, 1H), 6.50 (s, 1H), 6.20 (t, J=8.4 Hz, 1H), 5.76 (m, 1H), 5.25 (t, J=7.5 Hz, 1H), 5.09 (d, J=7.2 Hz, 1H), 5.04 (d, J=7.2 Hz, 1H), 4.79 (m, 1H), 4.48 (d, J=8.1 Hz, 1H), 4.20 (d, J=8.1 Hz, 1H), 3.66 (d, J=6.6 Hz, 1H), 3.55 (d, J=5.4 Hz, 1H), 2.43 (s, 3H), 2.31 (m, 2H), 2.21 (s, 3H), 1.97 (s, 3H), 1.82 (s, 3H), 1.76 (s, 1H), 1.21 (s, 3H), 1.17 (s, 3H).

Anal Calcd for C$_{47}$H$_{49}$NO$_{17}$S: C, 60.57; H, 5.30; N, 1.50. Found: C, 60.37; H, 5.39; N, 1.48.

To a solution of the 2'-hydroxy cyclic sulfate (4.956 g, 5.32 mmol) in 200 mL of methylene chloride and 5 mL of methanol was added Bu$_4$NBH$_4$ (1.367 g, 5.32 mmol) and stirred overnight. The solution was diluted with ethyl acetate and washed with aqueous NH$_4$Cl and then brine. The solution was dried over MgSO$_4$ and concentrated. The residue was chromatographed over silica gel using acetonitrile/ methylene chloride (15:85) to give 2.856 g of 13 (81%).

IR (KBr) 1721, 1396, 1248, 1210, 979 cm$^{-1}$ $^1$H NMR (300 MHz, CDCl$_3$) δ 8.09 (d, J=6.9 Hz, 2H), 7.63 (m, 1H), 7.50 (t, J=7.8 Hz, 2H), 6.55 (s, 1H), 5.71 (d, J=6.8 Hz, 1H), 5.30 (t, J=7.2 Hz, 1H), 5.12 (t, J=7.2 Hz, 2H), 4.85 (m, 1H), 4.48 (d, J=8.1 Hz, 1H), 4.15 (d, J=8.1 Hz, 1H), 3.76 (d, J=6.9 Hz, 1H), 2.31 (s, 3H), 2.27 (m, 2H), 2.22 (s, 3H), 2.07 (s, 3H), 1.95 (s, 3H), 1.61 (s, 1H), 1.24 (s, 1H), 1.33 (s, 3H), 1.07 (s, 3H).

EXAMPLE 17

Preparation of 2-O-Triethylsilyl-3'N-desbenzoyl-3'N-t-Butoxycarbonyl-6,7β-Paclitaxelsulfate [14].

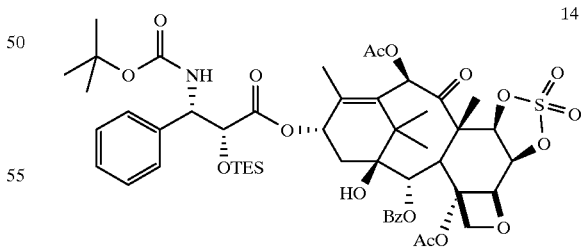

To a solution of the baccatin sulfate 13 (2.843 g, 4.28 mmol) in 50 mL of THF at −60° C. was added LiHMDS (5.2 mL, 1.0 M in THF, 5.2 mmol). After stirring in the cold for 15 minutes the lactam (2.629 g, 6.96 mmol) in 50 mL of THF was added dropwise. The solution was warmed to 0° C. for 30 minutes and diluted with ethyl acetate. The solution was washed with aqueous NH$_4$Cl and then brine, dried over MgSO$_4$, and concentrated. The residue was chromatographed over silica gel using hexane/ ethyl acetate (3:1) to give 3.970 g of 14 (89%).

ESIMS m/z 1040 (M–H)

IR (KBr) 1755, 1727, 1402, 1240, 1164, 981 cm$^{-1}$ $^1$H NMR (300 MHz, CDCl$_3$) δ 8.10 (d, J=7.2 Hz, 2H), 7.62 (m, 1H), 7.50 (t, J=7.8 Hz, 2H), 7.39–7.23 (m, 5H), 6.54 (s, 1H), 6.25 (t, J=8.4 Hz, 1H), 5.78 (d, J=6.9 Hz, 1H), 5.44 (d, J=9 Hz, 1H), 5.28 (t, J=7.2 Hz, 1H), 5.24 (br s, 1H), 5.13 (d, J=7.2 Hz, 1H), 5.07 (d, J=7.2 Hz, 1H), 4.53 (s, 1H), 4.50 (d, J=8.4 Hz, 1H), 4.19 (d, J=8.4 Hz, 1H), 3.70 (d, J=6.9 Hz, 1H), 2.56 (s, 3H), 2.29 (m, 2H), 2.21 (s, 3H), 1.97 (s, 3H), 1.91 (s, 3H), 1.67 (s, 1H), 1.30 (s, 9H), 1.25 (s, 3H), 1.17 (s, 3H), 0.77 (t, J=8.1 Hz, 1H), 0.38 (m, 6H).

Anal Calcd for C$_{51}$H$_{67}$NO$_{18}$SSi: C, 58.77; H, 6.48; N, 1.34. Found: C, 58.75; H, 6.60; N, 1.30.

EXAMPLE 18

Preparation of 3'N-desbenzoyl-3'N-t-Butoxycarbonyl-6,7β-Paclitaxelsulfate [15].

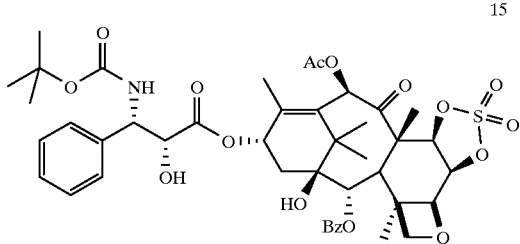

To a solution of the 2'-O-TES cyclic sulfate 14 (3.938 g, 3.78 mmol) at 0° C. was added 50 mL of 1N HCl. The solution was diluted with ethyl acetate and washed with NaHCO$_3$ and brine. The organic fraction was dried over MgSO$_4$ and concentrated. The residue was chromatographed over silica gel using hexane/ ethyl acetate (1:1) to give 3.607 g (quant).

ESIMS m/z: 926 (M–H)

IR (KBr) 1727, 1240, 1212, 979 cm$^{-1}$ $^1$H NMR (300 MHz, CDCl$_3$) δ 8.08 (d, J=7.2 Hz, 2H), 7.65–7.30 (m, 8H), 6.52 (s, 1H), 6.18 (t, J=8.1 Hz, 1H), 5.76 (d, J=6.9 Hz, 1H), 5.35 (br d, J=9.3 Hz, 1H), 5.27–5.20 (m, 2H), 5.09 (d, J=7.5 Hz, 1H), 5.05 (d, J=7.5 Hz, 1H), 4.61 (s, 1H), 4.47 (d, J=8.4 Hz, 1H), 4.16 (d, J=8.4 Hz, 1H), 3.66 (d, J=6.9 Hz, 3.33 (s, 1H), 2.41 (s, 3H), 2.32 (m, 2H), 2.21 (s, 3H), 1.95 (s, 3H), 1.86 (s, 3H), 1.72 (s, 1H), 1.33 (s, 9H), 1.22 (s, 3H), 1.17 (s, 3H).

Anal Calcd for C$_{45}$H$_{53}$NO$_{18}$S: C, 58.24; H, 5.76; N, 1.51. Found: C, 58.14; H, 5.93; N, 1.46.

EXAMPLE 19

Preparation of 3'N-desbenzoyl-3'N-t-Butoxycarbonyl-6α-Fluoropaclitaxel [Ik].

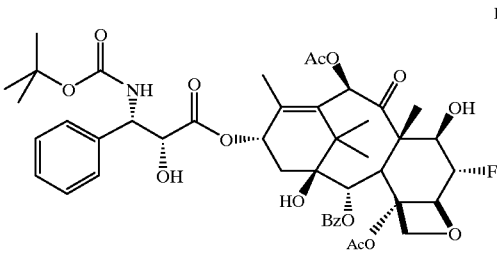

To a solution of the cyclic sulfate 15 (1.00 g, 1.077 mmol) in 15 mL of THF was added Triethylamine trishydrofluoride (0.59 mL) and Bu$_4$ NF (5.38 mL, 1.0 M in THF, 5.38 mmol). The solution was heated to 70° C. for 2 hours, cooled, and diluted with ethyl acetate. The solution was washed with NaHCO$_3$, brine, dried over MgSO$_4$, and concentrated. The residue in 20 mL of THF was stirred with 180 μL of water and 0.5 mL of concentrated H$_2$SO$_4$ for 45 minutes. The solution was diluted with ethyl acetate and washed with NaHCO$_3$, brine, dried over MgSO$_4$, and concentrated. The residue was chromatographed over silica gel using hexane and ethyl acetate (1:1) to give 801 mg of fluoride (86%).

ESIMS m/z 868 (M+H)

IR (KBr) 3445, 1720, 1370, 1243, 1169, 1105, 1071, 986 cm$^{-1}$ $^1$H NMR (300 MHz, CDCl$_3$) δ 8.09 (d, J=7.2 Hz, 2H), 7.64–7.29 (m, 8H), 6.30 (s, 1H), 6.23 (t, J=8.7 Hz, 1H), 5.64 (d, J=6.9 Hz, 1H), 5.35 (br d, J=9.3 Hz, 1H), 5.26 (br d, 1H), 4.96 (d, J=25 Hz, 1H), 4.70 (dd, J=49, 8 Hz, 1H), 4.63 (m, 1H), 4.45 (ddd, J=17.1, 11.7, 3.3 Hz, 1H), 4.30 (d, J=8.4 Hz, 1H), 4.16 (d, J=8.4 Hz, 1H), 3.96 (d, J=6.9 Hz, 1H), 3.28 (br d, 1H), 2.85 (d, J=3.6 Hz, 1H), 2.40 (s, 3H), 2.29 (d, J=8.7 Hz, 2H), 2.24 (s, 3H), 1.86 (s, 3H), 1.66 (s, 1H), 1.64 (s, 3H), 1.32 (s, 9H), 1.26 (s, 3H), 1.13 (s, 3H).

Anal Calcd for C$_{45}$H$_{54}$FNO$_{15}$: C, 62.27; H, 6.27; N, 1.61. Found: C, 62.05; H, 6.28; N, 1.57.

EXAMPLE 20

Preparation of 2-O-Triethylsilyl-3'N-desbenzoyl-3'N-t-Butoxycarbonyl-6α-Fluoropaclitaxel [16].

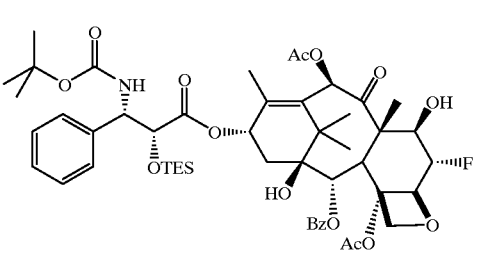

To a solution of the fluoride Ik (800 mg, 0.923 mmol) in 10 mL of methylene chloride was added 10 mL of pyridine and TESCl (1.2 mL, 7.2 mmol) and stirred at 0° C. for 4 hours. The solution was diluted with ethyl acetate and washed with water 3 times and brine. The solution was then dried over MgSO$_4$, concentrated, and the residue chromatographed over silica gel using hexane/ ethyl acetate (2:1) to give 845 mg (93%) of the 2-O-TES ether 16.

ESIMS m/z 980 (M–H)

IR (KBr) 3449, 1755, 1734, 1720, 1243 cm$^{-1}$ $^1$H NMR (300 MHz, CDCl$_3$) δ 8.10 (d, J=7.2 Hz, 2H), 7.63–7.24 (m, 8H), 6.31 (s, 1H), 6.29 (t, J=9.3 Hz, 1H), 5.66 (d, J=6.9 Hz, 1H), 5.47 (br d, J=9.6 Hz, 1H), 5.28 (br d, J=8.1 Hz, 1H), 5.02 (d, J=25.7 Hz, 1H), 4.72 (dd, J=49.2, 8.4 Hz, 1H), 4.50 (m, 2H), 4.33 (d, J=8.4 Hz, 1H), 4.18 (d, J=8.4 Hz, 1H), 3.99 (d, J=6.9 Hz, 1H), 2.86 (br s, 1H), 2.54 (s, 3H), 2.39 (m, 1H), 2.23 (s, 4H), 1.92 (s, 3H), 1.68 (s, 1H), 1.65 (s, 3H), 1.30 (s, 9H), 1.28 (s, 3H), 1.13 (s, 3H), 0.76 (t, J=8.1 Hz, 9H), 0.36 (m, 6H).

Anal Calcd for C$_{50}$H$_{68}$FNO$_{15}$Si: C, 62.37; H, 6.98; N, 1.43. Found: C, 62.27; H, 6.98; N, 1.51.

EXAMPLE 21

Preparation of 3'N-desbenzoyl-3'N-t-Butoxycarbonyl-7-O-methoxymethyl-6a-Fluoropaclitaxel [I1].

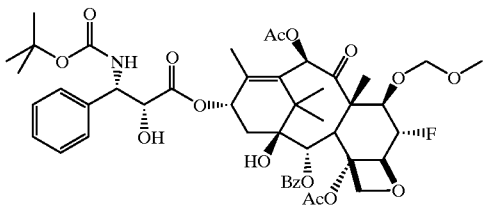

To a solution of the 2-O-TES ether 16 (635 mg, 0.646 mmol) in 20 mL of methylene chloride was added diisopropylethyl amine (3.38 mL, 19.4 mmol) and chloromethyl methyl ether (1.41 mL, 19.4 mmol) and the solution stirred for 2 days. The solution was diluted with ethyl acetate and washed with NaHCO$_3$ and brine. The solution was dried over MgSO$_4$, concentrated, and chromatographed over silica gel using hexane/ ethyl acetate to give 600 mg of 2'-O-TES-7-O-MOM.

The 2'-O-TES ether in 10 mL of acetonitrile was stirred at 0° C. with 7 mL of 1N HCl. The solution was diluted with ethyl acetate and washed with NaHCO$_3$ and brine. The solution was dried over MgSO$_4$, concentrated, and chromatographed over silica gel using hexane/ ethyl acetate (1:1) to give 520 mg of 7O-MOM ether I1 (87%).

ESIMS m/z 934 (M+Na)

IR (KBr) 3493, 3374, 1754, 1721, 1715, 1249 cm$^{-1}$ $^1$H NMR (300 MHz, CDCl$_3$) δ 8.08 (d, J=7.2 Hz, 1H), 7.64–7.31 (m, 8H), 6.55 (s, 1H), 6.19 (t, J=9 Hz, 1H), 5.66 (d, J=6.9 Hz, 1H), 5.38 (d, J=9.3 Hz, 1H), 5.26 (br d, J=9 Hz, 1H), 4.94 (d, J=26.1 Hz, 1H), 4.84 (dd, J=49.2, 7.7 Hz, 1H), 4.82 (d, J=6.6 Hz, 1H), 4.68 (d, J=6.6 Hz, 1H), 4.63 (br s, 1H), 4.26 (m, 2H), 4.15 (d, J=8.4 Hz, 1H), 4.01 (d, J=6.9 Hz, 1H), 3.32 (d, J=5.4 Hz, 1H), 3.29 (s, 3H), 2.39 (s, 3H), 2.30 (d, J=9 Hz, 2H), 2.19 (s, 3H), 2.00 (s, 3H), 1.66 (s, 1H), 1.57 (s, 3H), 1.34 (s, 9H), 1.21 (s, 3H), 1.19 (s, 3H).

Anal Calcd for C$_{47}$H$_{58}$FNO$_{16}$: C, 61.90; H, 6.41; N, 1.54. Found: C, 61.81; H, 6.48; N, 1.51.

EXAMPLE 22

Preparation of 3'N-desbenzoyl-3'N-t-Butoxycarbonyl-7-O-methylthiomethyl-6α-Fluoropaclitaxel [Im].

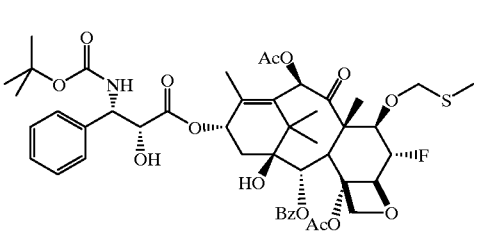

To a solution of the 2'-O-TES ether 16 (1.046 g, 1.065 mmol) at 0° C. was added dimethyl sulfide (0.78 mL, 10.65 mmol) and benzoyl peroxide (1.288 g, 5.325 mmol). The solution was stirred at 0° C. for 3 hours. The solution was diluted with ethyl acetate and washed with NaHCO$_3$ and brine. The solution was dried over MgSO$_4$, concentrated, and chromatographed over silica gel.

The residue in 20 mL of acetonitrile at 0° C. was added 10 mL of 1N HCl. The solution was diluted with ethyl acetate and washed with NaHCO$_3$ (3×) and brine. The organic fraction was dried over MgSO$_4$, concentrated, and the residue chromatographed over silica gel using hexane/ ethyl acetate (3:2) to give 711 mg of Im (72%).

ESIMS m/z 926 (M–H)

IR (KBr) 3507, 1728, 1717, 1269, 1230, 993 cm$^{-1}$ $^1$H NMR (300 MHz, CDCl$_3$) δ 8.09 (d, J=7.2 Hz, 2H), 7.64–7.31 (m, 8H), 6.68 (s, 1H), 6.20 (t, J=9 Hz, 1H), 5.65 (d, J=6.9 Hz, 1H), 5.37 (d, J=9.6 Hz, 1H), 5.26 (br d, J=9 Hz, 1H), 4.93 (dd, J=49.2, 7.8 Hz, 1H), 4.92 (d, J=27.3 Hz, 1H), 4.89 (s, 2H), 4.64 (br s, 1H), 4.45 (dd, J=16.5, 7.8 Hz, 1H), 4.30 (d, J=8.4 Hz, 1H), 4.15 (d, J=8.4 Hz, 1H), 4.03 (dd, J=16.5, 7.8, 1H), 3.30 (br s, 1H), 2.40 (s, 3H), 2.31 (d, J=9 Hz, 2H), 2.18 (s, 3H), 2.12 (s, 6H), 2.07 (s, 3H), 1.69 (s, 3H), 1.61 (s, 1H), 1.34 (s, 9H), 1.20 (s, 6H).

Anal Calcd for C$_{47}$H$_{58}$FNO$_{15}$S C, 60.85; H, 6.30; N, 1.51. Found: C, 60.86; H, 6.34; N, 1.47.

EXAMPLE 23

Preparation of 3'N-desbenzoyl-3'N-t-Butoxycarbonyl-7-O-methyl-6α-Fluoropaclitaxel [In].

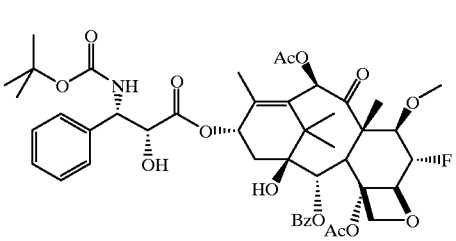

To a solution of Im (711 mg, 0.768 mmol) in 40 mL of ethanol was added Raney Nickel (washed with water until neutral by pH paper, 5 g). The suspension was heated to 80° C. for 4 hours. The solution was filtered through Celite and concentrated. The residue was dissolved in ethyl acetate and washed with brine (2×), dried over MgSO$_4$, and concentrated. The residue was chromatographed over silica gel using hexane/ ethyl acetate (3:2) to give 495 mg of In (73%).

ESIMS m/z 880 (M–H)

IR (KBr) 3534, 3480, 3452, 1743, 1731, 1717, 1264, 1228 cm$^{-1}$ $^1$H NMR (300 MHz, CDCl$_3$) δ 8.08 (d, J=7.2 Hz, 2H), 7.64–7.29 (m, 8H), 6.42 (s, 1H), 6.19 (t, J=9 Hz, 1H), 5.62 (d, J=6.9 Hz, 1H), 5.38 (br d, J=9.3 Hz, 1H), 5.27 (br d, J=9 Hz, 1H), 4.92 (d, J=26.4 Hz, 1H), 4.85 (dd, J=41.7, 7.8 Hz, 1H), 4.62 (br s, 1H), 4.29 (d, J=8.4 Hz, 1H), 4.13 (d, J=8.4 Hz, 1H), 3.99 (d, J=6.9 Hz, 1H), 3.94 (dd, J=16.8, 7.8 Hz, 1H), 3.55 (s, 3H), 3.32 (d, J=5.1 Hz, 1H), 2.39 (s, 3H), 2.31 (d, J=9 Hz, 2H), 2.22 (s, 3H), 1.93 (s, 3H), 1.65 (s, 1H), 1.64 (s, 3H), 1.34 (s, 9H), 1.23 (s, 3H), 1.18 (s, 3H).

EXAMPLE 24

2'-O-(triethylsilyl)-7-deoxy-6α-triflouromethanesulphonyloxypaclitaxel [17]

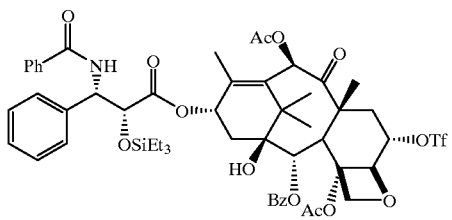

The diol 4 (1.773 g, 1.809 mmol), thiocarbonyldiimidazole (0.996 g, 5.427 mmol), DMAP (0.618 g, 5.065 mmol) were dissolved in 50 mL THF and allowed to stir overnight. The reaction was diluted with EtOAc, washed with NaHCO$_3$, and brine. The solution was dried over MgSO$_4$, filtered, and concentrated. The residue was chromatographed over silica gel (1:1 hexane/ethyl acetate) to yield 1.646 g of product 18 (89%).

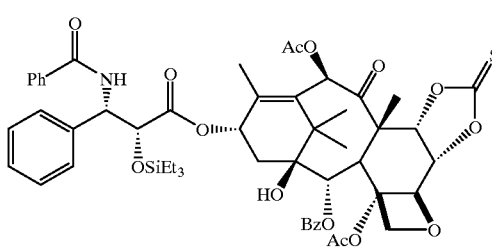

ESILRMS m/z 1043 (M=NH$_4$).

IR(KBr) 3438(br.), 2958, 1746, 1717, 1282, 1236 cm$^{-1}$ $^1$H NMR (CDCl$_3$, 300 MHz) d 8.15(d, J=7.2 Hz, 2H), 7.74 (d, J=7.2 Hz, 2H), 7.63–7.32(m, 11H), 7.12(d, J=9.0 Hz, 1H), 6.87(s, 1H), 6.25(br. t., 1H), 5.83(d, J=6.9 Hz, 1H), 5.70(d, J=9.0, 1H), 4.97(d, J=11.4 Hz, 1H), 4.87(s, 1H), 4.72(m, 2H), 4.39(d, J=8.1 Hz, 1H), 4.22(d, J=8.1 Hz, 1H), 4.00(D, J=6.9 Hz, 1H), 2.57(s, 3H), 2.43–2.35(m, 1H), 2.21(s, 3H), 2.16–2.08(m, 1H), 2.03(m, 4H), 1.87(s, 3H), 1.21(s, 3H), 1.17(s, 3H), 0.79(m, 9H), 0.44(m, 6H).

Anal. calcd. for C$_{54}$H$_{63}$O$_{15}$N S Si: C, 63.20; H, 6.19; N, 1.36. Found: C, 63.04; H, 6.22; N, 1.33.

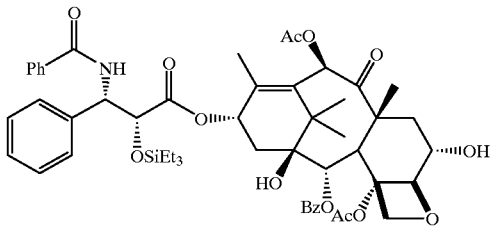

The thiocarbonate 18 (0.200 g, 0.196 mmol), AIBN(cat.), (aza-isobutyrylnitrile (catalytic)) and Bu$_3$GeH(0.479 g, 1.96 mmol) were dissolved in 3 mL toluene under Argon. The reaction mixture was frozen, dried in vacuo, and thawed three times to remove O$_2$. The reaction was heated to 85° C. for 1 hr.. The reaction mixture was concentrated and chromatographed over silica gel (1.5:1 hexane/ethyl acetate) to yield 0.137 g of product 19 (72%).

ESILRMS m/z 968 (M+H).

IR(KBr) 3442(br.), 2956, 1734, 1486, 1372, 1244, 710 cm$^{-1}$.

$^1$H NMR (CDCl$_3$, 300 MHz) d 8.13(d, J=8.7 Hz, 2H), 7.72(d, J=8.4 Hz, 2H), 7.62–7.33(m, 11H), 7.10(d, J=8.7 Hz, 1H), 6.45(s, 1H), 6.24(t, J=8.7 Hz, 1H), 5.71–5.64(m, 2H), 4.80(s, 1H), 4.66(d, J=2.1 Hz, 1H), 4.31(d, J=8.4 Hz, 1H), 4.18–4.14(m, 2H), 3.78(d, J=7.5 Hz, 1H), 2.54(s, 3H), 2.48–2.39(m, 1H), 2.20(s, 3H), 2.17–2.08(m, 1H), 2.02(d, J=9.0 Hz, 2H), 1.90(s,4H), 1.77(s, 1H), 1.71(s, 3H), 1.19(s, 3H), 1.10(s, 3H), 0.79(m, 9H), 0.41(m,6H).

Anal. calcd. for C$_{53}$H$_{65}$O$_{14}$NSi·H$_2$O: C, 64.55; H, 6.85; N, 1.42. Found: C, 64.49; H, 6.82; N, 1.41.

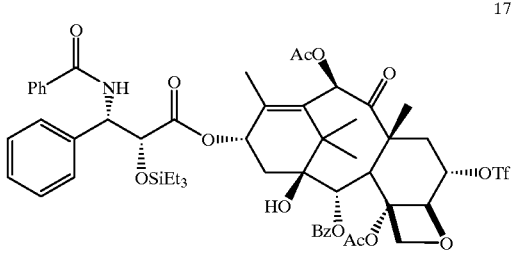

The alcohol 19 (0.950 g, 0.98 mmol) and DMAP (0.479 g, 3.92 mmol) were dissolved in 10 mL of dichloromethane and cooled to 0° C. under nitrogen. Triflic anhydride (198 μL, 1.18 mmol) was added via syringe, and the reaction was allowed to stir at 0° C. for 10 min. The crude reaction mixture was placed directly onto a vacuum funnel containing a 1.5 inch plug of silica gel wet with hexanes, and eluted with (3:1 hexanes / ethyl acetate) to provide the triflate 17 (0.842 g 78%) as a white powder.

ESIMS m/z 1099 (M–H)

IR (KBr) 3442, 2957, 1748, 1735, 1725, 1245, 1225, 1143 cm$^{-1}$ $^1$H NMR (CDCl$_3$ 300 MHz) δ 8.13 (d, J=7.2 Hz, 2H), 7.72 (d, J=7.2 Hz, 2H), 7.50–7.25 (m, 11H), 7.10 (d, J=9.1Hz, 1H), 6.41 (s, 1H), 6.25 (t, J=8.6 Hz, 1H), 5.73 (d, J=9.0 Hz, 1H), 5.64 (d, J=7.5 Hz, 1H), 5.22 (dd, J=11.7, 7.5 Hz, 1H), 4.98 (s, 1H), 4.68 (d, J=2.0 Hz, 1H), 4.33 (d, J=8.5 Hz, 1H), 4.26 (d, J=8.6 Hz, 1H), 3.89 (d, J=7.4 Hz, 1H), 2.58 (s, 3H, 2.50–2.40 (m, 2H), 2.21 (s, 3H), 2.19–2.04 (m, 2H), 1.92 (s, 3H), 1.71 (s, 3H), 1.21 (s, 3H), 1.10 (s, 3H), 0.78 (m, 9H), 0.43 (m, 6H)

EXAMPLE 25

Preparation of 2'-O-Tiethylsilyl-7-Deoxy-6-β-Chloropaclitaxel (20)

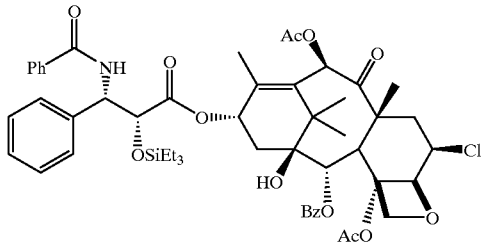

20

To a solution of the 6-α-triflate 17 (505 mg, 0.459 mmol) in 10 mL of THF was added Bu$_4$NCl·H$_2$O (390 mg, 1.40 mmol) and the solution stirred for 3 days. The solution was concentrated and the residue chromatographed over silica gel using hexane/ ethyl acetate (3:1) to give 396 mg of product. An analytical sample was crystalized from ether/hexane to give an amorphous white powder.

ESIMS m/z 986 (M-H)

IR (KBr) 3441, 1748, 1731, 1722, 1238 cm$^{-1}$ $^1$H NMR (CDCl$_3$ 300 MHz) δ: 8.14 (d, J=7.2 Hz, 2H), 7.73 (d, J=7.2 Hz, 2H), 7.66–7.25 (m, 11H), 7.05 (d, J=9.1 Hz, 1H), 6.41 (s, 1H), 6.25 (t, J=8.4 Hz, 1H), 5.75 (m, 2H), 4.91 (d, J=5.4 Hz, 1H), 4.63 (m, 2H), 4.37 (d, J=8.4 Hz, 1H), 4.18 (d, J=8.4 Hz, 1H), 3.75 (d, J=6.6 Hz, 1H), 2.57 (s, 3H), 2.50 (m, 1H), 2.34 (m, 1H), 2.21 (s, 3H), 2.11 (m, 2H), 1.95 (s, 3H), 1.88 (s, 3H), 1.85 (s, 1H), 1.21 (s, 3H), 1.11 (s, 3H), 0.81 (t, J=7.8 Hz, 9H), 0.42 (m, 6H).

Anal. calcd. for C$_{55}$H$_{64}$ClNO$_{13}$Si: C, 65.36; H, 6.38; N, 1.39. Found: C, 64.42; H, 6.59; N, 1.29.

EXAMPLE 26

Preparation of 7-Deoxy-6-β-Chloropaclitaxel (Io)

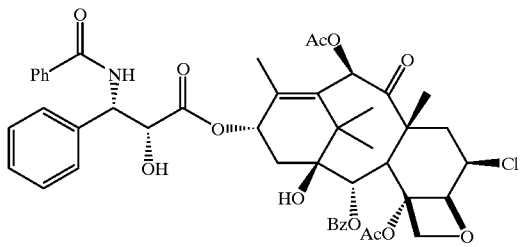

Io

To a solution of the 2'-O-triethylsilyl ether 20 (446 mg, 0.453 mmol) in 15 mL of THF was added Bu$_4$NF (0.50 mL, 1.0 M in THF, 0.50 mmol) and Et$_3$N·3HF (50 μL) and the solution stirred at 0° C. for 2 hours. The solution was concentrated and the residue chromatographed over silica gel using hexane/ ethyl acetate (1:1) to give 320 mg of product. The product was crystalized from ethyl acetate/hexane to give a white amorphous powder which was 93% pure by HPLC analysis.

ESIMS m/z 870 (M-H)

IR (KBr) 3435, 1727, 1271, 1238, 1107, 1071 cm$^{-1}$ $^1$H NMR (CDCl$_3$ 300 MHz) δ: 8.13 (d, J=7.2 Hz, 2H), 7.74 (d, J=7.2 Hz, 2H), 7.64–7.31 (m, 11H), 7.03 (d, J=9 Hz, 1H), 6.37 (s, 1H), 6.18 (t, J=9 Hz, 1H), 5.76 (m, 2H), 4.89 (d, J=5.1 Hz, 1H), 4.78 (m, 1H), 4.59 (m, 1H), 4.36 (d, J=8.4 Hz, 1H), 4.16 (d, J=8.4 Hz, 1H), 3.75 (d, J=6.6 Hz, 1H), 3.62 (d, J=4.8 Hz, 1H), 2.47 (m, 1H), 2.38 (s, 3H), 2.28 (m, 2H), 2.22 (s, 3H), 2.10 (m, 1H), 1.93 (s, 3H), 1.86 (s, 1H), 1.74 (s, 3H), 1.20 (s, 3H), 1.12 (s, 3H).

Anal. calcd. for C$_{47}$H$_{50}$ClNO$_{13}$: C, 64.71; H, 5.78; N, 1.61 Found: C, 64.58; H, 5.92; N, 1.51.

EXAMPLE 27

Preparation of 7-Deoxy-6-β-Bromopaclitaxel (Ip)

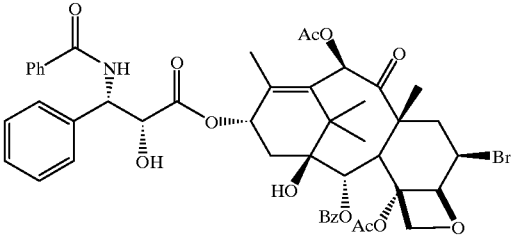

Ip

To a solution of the 6α-triflate 20 (610 mg, 0.555 mmol) in 20 mL of toluene was added Bu$_4$NBr (644 mg, 2.0 mmol) and the solution stirred for 3 hours. The solution was concentrated and the residue dissolved in 20 mL of THF and stirred for 1 day with Et$_3$N·3HF (221 μL, 1.354 mmol). The solution was diluted with ethyl acetate and washed with water and brine, dried over MgSO$_4$ and concentrated. The residue was chromatographed over silica gel using hexane/ ethyl acetate (1.25:1) and then crystalized from ethyl acetate/ hexane to give 405 mg (79%) of a white amorphous solid which was 92.5% pure by HPLC analysis.

ESIMS m/z 916 (M+H)

IR (KBr) 3439, 1726, 1372, 1270, 1239, 1107, 1071 cm$^{-1}$ $^1$H NMR (CDCl$_3$ 300 MHz) δ: 8.12 (d, J=7.2 Hz, 2H), 7.75 (d, J=7.2 Hz, 2H), 7.65–7.31 (m, 11H), 7.04 (d, J=9 Hz, 1H), 6.36 (s, 1H), 6.18 (t, J=8.7 Hz, 1H), 5.78 (m, 2H), 4.88 (d, J=4.5 Hz, 1H), 4.78 (m, 1H), 4.66 (m, 1H), 4.33 (d, J=8.4 Hz, 1H), 4.16 (d, J=8.4 Hz, 1H), 3.78 (d, J=6.6 Hz, 1H), 3.63 (d, J=4.5 Hz, 1H), 2.56 (m, 1H), 2.38 (s, 3H), 2.27 (m, 3H), 2.22 (s, 3H), 1.95 (s, 3H), 1.87 (s, 1H), 1.74 (s, 3H), 1.21 (s, 3H), 1.11 (s, 3H).

Anal. calcd. for C$_{47}$H$_{50}$BrNO$_{13}$: C, 61.57; H, 5.50; N, 1.53. Found: C, 61.17; H, 6.01; N, 1.55.

EXAMPLE 28

Preparation of 7-Deoxy-6-β-Iodopaclitaxel (Iq)

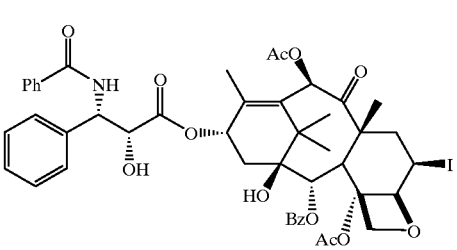

Iq

To a solution of the 6α-triflate 20 (614 mg, 0.558 mmol) in 20 mL of THF was added Bu$_4$NI (742 mg, 2.0 mmol) and the solution stirred for 5 days. The solution was diluted with ethyl acetate and washed with water and brine, dried over MgSO$_4$ and concentrated. The residue was in 20 mL of THF and treated with Bu$_4$NF (0.614 mL, 1.0 M in THF, 0.614 mmol) and Et$_3$N·3HF (60 μL) at ambient temperature for 3 hours. The solution was concentrated and the residue chromatographed over silica gel using hexane/ ethyl acetate (1.25:1) and the residue crystalized from ethyl acetate/ hexane to give 346 mg (64%) of white amorphous solid.

ESIMS m/z 964 (M–H)

IR (KBr) 3441, 1727, 1271, 1238, 1108, 1071 cm$^{-1}$ $^1$H NMR (CDCl$_3$ 300 MHz) δ: 8.11 (d, J=7.2 Hz, 2H), 7.75 (d, J=7.2 Hz, 2H), 7.64–7.31 (m, 11H), 7.05 (d, J=9 Hz, 1H), 6.35 (s, 1H), 6.17 (t, J=7.2 Hz, 1H), 5.79 (d, J=8.7 Hz, 1H), 5.74 (d, J=6.6 Hz, 1H), 4.79 (m, 3H), 4.28 (d, J=8.4 Hz, 1H), 4.11(d, J=8.4 Hz, 1H), 3.80 (d, J=6.3 Hz, 1H), 3.65 (d, J=4.8 Hz, 1H), 2.61 (m, 1H), 2.45–2.25 (m, 3H), 2.37 (s, 3H), 2.21 (s, 3H), 1.96 (s, 3H), 1.88 (s, 1H), 1.74 (s, 3H), 1.20 (s, 3H), 1.11 (s, 3H).

Anal. calcd. for C$_{47}$H$_{50}$INO$_{13}$: C, 58.57; H, 5.23; N,1.45. Found: C, 58.36; H, 5.31; N, 1.27.

EXAMPLE 29

Preparation of 6-β-Chloro-7-deoxybaccatin [21].

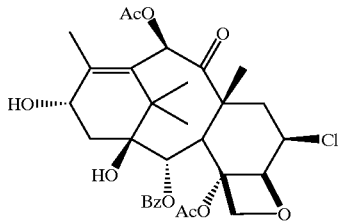

To a solution of Io (1.0 g, 1.15 mmol) in 25 mL of methylene chloride was added 2 mL of methanol and Bu$_4$NBH$_4$ (447 mg, 1.73 mmol). The solution was stirred for 3 days at ambient tempterature. The solution was diluted with ethyl acetate and washed with NH$_4$Cl solution and brine. The organic fraction was dried over MgSO$_4$, concentrated, and the residue chromatographed over silica gel using hexane/ ethyl acetate (1:1) and then chromatographed a second time using methylene chloride/ ethyl acetate (3:1) to give 234 mg of 21 (33%).

ESIMS m/z 603 (M–H)

IR (KBr) 3524, 1731, 1716, 1272, 1234, 1072 cm$^{-1}$ $^1$H NMR (300 MHz, CDCl$_3$) δ 8.10 (d, J=7.8 Hz, 2H), 7.61 (m, 1H), 7.48 (t, J=7.8 Hz, 2H), 6.42 (s, 1H), 5.69 (d, J=6.9 Hz, 1H), 4.89 (d, J=6 Hz, 1H), 4.83 (br m, 1H), 4.63 (m, 1H), 4.35 (d, J=7.8 Hz, 1H), 4.10 (ABq, J=14.4, 6.9 Hz, 2H), 3.81 (d, J=6.9 Hz, 1H), 2.54 (dd, J=15.6, 8.4 Hz, 1H), 2.29 (s, 3H), 2.24 (m, 1H), 2.22 (s, 3H), 2.10 (m, 2H), 2.02 (s, 3H), 1.90 (s, 3H), 1.67 (s, 1H), 1.08 (s, 6H).

Anal Calcd for C$_{31}$H$_{37}$ClO$_{10}$: C, 61.54; H, 6.16. Found: C, 61.54; H, 6.08.

EXAMPLE 30

Preparation of 3'N-desbenzoyl-3'N-t-Butoxycarbonyl-6β-Chloro-7-Deoxypaclitaxel [Ir].

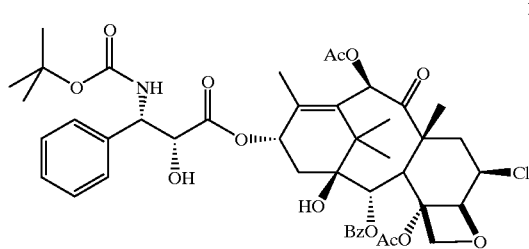

To a solution of 21 (234 mg, 0.387 mmol) in 5 mL of THF at –60° C. was added LiHMDS (425 μL, 1.0 M in THF, 0.425 mmol) and stirred 10 minutes. A solution of β-lactam (233 mg, 0.616 mmol) in 5 mL of THF was added dropwise and the solution warmed to 0° C. The solution was diluted with ethyl acetate and washed with NH$_4$Cl solution and brine. The organic fraction was dried over MgSO$_4$, concentrated, and the residue chromatographed over silica gel using hexanel ethyl acetate (4:1) to give 305 mg of coupling product.

The product was desilylated in 15 mL of acetonitrile at 0° C. with 74 μL of 1N HCl for 1 hour. The solution was stirred with solid NaHCO$_3$, diluted with ethyl acetate, and dried over MgSO$_4$. The ethyl acetate solution was concentrated and the residue chromatographed over silica gel using hexane/ethyl acetate (3:2) to give 270 mg of Ir (80%).

IR (KBr) 3445, 1733, 1716, 1270, 1237, 1169 cm$^{-1}$ $^1$H NMR (300 MHz, CDCl$_3$) δ 8.10 (d, J=7.2 Hz, 2H), 7.64–7.28 (m, 8H), 6.40 (s, 1H), 6.18 (t, J=9 Hz, 1H), 5.74 (d, J=6.9 Hz, 1H), 5.39 (br d, J=9.3 Hz, 1H), 5.25 (br d, J=9 Hz, 1H), 4.89 (d, J=5.3 Hz, 1H), 4.60 (m, 2H), 4.35 (d, J=7.8 Hz, 1H), 4.13 (d, J=7.8 Hz, 1H), 3.75 (d, J=6.9 Hz, 1H), 3.37 (d, J=5.1 Hz, 1H), 2.49 (dd, J=15.3, 8.4 Hz, 1H), 2.37 (s, 3H), 2.22 (s, 3H), 2.22 (m, 2H), 2.11 (dd, J=15.3, 9.6 Hz, 1H), 1.92 (s, 3H), 1.80 (s, 3H), 1.76 (s, 1H), 1.33 (s, 9H), 1.23 (s, 3H), 1.13 (s, 3H).

Anal Calcd for C$_{45}$H$_{54}$ClNO$_{14}$: C, 62.24; H. 6.27; N, 1.61. Found: C, 62.41; H. 6.21; N. 1.57.

EXAMPLE 31

Preparation of 3'N-desbenzoyl-3'N-i-Propoxycarbonyl-6β-Chloro-7-Deoxypaclitaxel [Is].

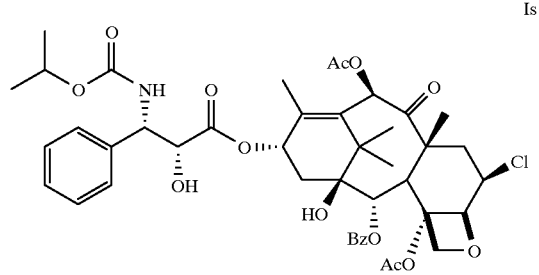

To a solution of 21 (643 mg, 1.063 mmol) in 10 mL of THF at –60° C. was added LiHMDS (1.3 mL, 1.0 M in THF, 1.3 mmol) and stirred 10 minutes. A solution of β-lactam (628 mg, 1.727 mmol) in 10 mL of THF was added dropwise and the solution warmed to 0° C. The solution was diluted with ethyl acetate and washed with NH$_4$Cl solution and brine. The organic fraction was dried over MgSO$_4$, concentrated, and the residue chromatographed over silica gel using hexane/ ethyl acetate (4:1) to give 838 mg of coupling product.

The product was desilylated in 10 mL of acetonitrile at 0° C. with 173 μL of 1N HCl for 1 hour. The solution was diluted with ethyl acetate, washed with NaHCO$_3$ solution and brine, and dried over MgSO$_4$. The ethyl acetate solution was concentrated and the residue chromatographed over silica gel using hexane/ethyl acetate (1:1) to give 712 mg of Is (78%).

ESIMS m/z 854 (M+H)

IR (KBr) 3443, 1739, 1717, 1269, 1238, 1109 cm$^{-1}$ $^1$H NMR (300 MHz, CDCl$_3$) δ 8.10 (d, J=7.2 Hz, 2H), 7.64–7.28 (m, 8H), 6.40 (s, 1H), 6.20 (t, J=8.4 Hz, 1H), 5.75 (d, J=6.6 Hz, 1H), 5.49 (br d, J=9.6 Hz, 1H), 5.28 (br d, 8.4 Hz, 1H), 4.88 (d, J=5.4 Hz, 1H), 4.78 (m, 1H), 4.60 (m, 2H), 4.35 (d, J=8.4 Hz, 1H), 4.13 (d, J=8.4 Hz, 1H), 3.74 (d, J=6.6 Hz, 1H), 3.40 (d, J=4.8 Hz, 1H), 2.49 (dd, J=15.6, 8.7 Hz, 1H), 2.37 (s, 3H), 2.24 (d, J=9.0 Hz, 2H), 2.22 (s, 3H), 2.11 (dd, J=15.3, 6 Hz, 1H), 1.93 (s, 3H), 1.79 (s, 3H), 1.75 (s, 1H), 1.22 (s, 3H), 1.12 (m, 9H).

Anal Calcd for C$_{44}$H$_{52}$ClNO$_{14}$: C, 61.86; H, 6.13; N, 1.64. Found: C, 61.59; H, 6.08; N, 1.55.

The compounds of this invention exhibit antitumor activities in in vivo and/or in vitro models. For example, the following test describes the in vivo test used to evaluate some representative compounds of this invention.

Cytoxicity (In-Vitro)

Cytoxicity was assessed in HCT-116 human colon carcinoma cells by MTS (3-(4,5-dimethylthiazol-2-yl)-5-(3-carboxymethoxyphenyl)-2-(4-sulphenyl)-2H-tetrazolium, inner salt) assay as reported in T. L. Riss, et. al., "Comparison of MTT, XTT, and a novel tetrazolium compound MTS for in vitro proliferation and chemosensitivity assays.," *Mol. Biol. Cell* 3 (Suppl.):184a, 1992. Cells were plated at 4,000 cell/well in 96 well microtiter plates and 24 hours later drugs were added and serial diluted. The cells were incubated at 37° form 72 hours at which time the tetrazolium dye, MTS at 333 μg/ml (final concentration), in combination with the electron coupling agent phenazine methosulfate at 25 μM (final concentration) was added. A dehydrogenase enzyme in live cells reduces the MTS to a form that absorbs light at 492 nM which can be quantitated spectrophotometrically. The greater the absorbance the greater the number of live cells. The results are expressed as an IC$_{50}$, which is the drug concentration required to inhibit cell proliferation (i.e. absorbance at 450 nM) to 50% of that of untreated control cells. The IC$_{50}$ values for compounds evaluated in this assay are evaluated in Table I.

TABLE I

| Compound | IC$_{50}$ (nM) HCT 116 |
| --- | --- |
| Ia (example 4) | 1.4 |
| Ib (example 6) | 1.3 |
| Ic (example 8) | 3.3 |
| Id (example 9) | 0.83 |
| Ie (example 10) | 2.6 |
| If (example 11) | 1.5 |
| Ih (example 13) | 7.35 |
| Ii (example 14) | 4.95 |
| Ij (example 15) | 1.2 |
| Ik (example 19) | 0.2 |
| Il (example 21) | 2.5 |
| Im (example 22) | 1.0 |
| Io (example 26) | 0.62 |
| Ip (example 27) | 0.72 |
| Iq (example 28) | 2.24 |
| paclitaxel | 1.53–2.73 |

Mice M109 Model (In-Vivo)

Balb/c x DBA/2 F$_1$ hybrid mice were implanted intraperitoneally, as described by William Rose in *Evaluation of Madison 109 Lung Carcinoma as a Model for Screening Antitumor Drugs, Cancer Treatment Reports,* 65, No. 3–4 (1981), with 0.5 mL of a 2% (w/v) brei of M109 lung carcinoma.

Mice were treated with compounds under study by receiving intraperitoneal injections of various doses on either days 1, 5 and 9 post-tumor implant or days 5 and 8 post-implant. Mice were followed daily for survival until approximately 75–90 days post-tumor implant. One group of mice per experiment remained untreated and served as the control group.

Median survival times of compound-treated (T) mice were compared to the median survival time of the control (C) mice. The ratio of the two values for each compound-treated group of mice was multiplied by 100 and expressed as a percentage (i.e. % T/C in the following Table II for representative compounds.

In-Vivo Biology

TABLE II

| Compound | % T/C ip M109 (dose mg/kg) |
| --- | --- |
| Ib (example 6) | 162 (100) |
| Ic (example 8) | 147 (100) |
| Id (example 9) | 147 (100) |
| Ie (example 10) | 214 (200) |
| If (example 11) | 132 (100) |
| Ih (example 13) | 132 (195) |
| Ii (example 14) | 141 (195) |
| Ij (example 15) | 203 (100) |
| Ik (example 19) | 269 (100) |
| Il (example 21) | 187 (50) |
| In (example 23) | 144 (25) |
| Io (example 26) | 166 (25) |
| Ip (example 27) | 172 (50) |
| Iq (example 28) | 129 (50) |

Thus, another aspect of the instant invention concerns a method for inhibiting human and/or other mammalian tumors which comprises administering to a tumor bearing host an antitumor effective amount of a compound of formula I.

For treating a variety of tumors, the compound of formula I of the present invention may be used in a manner similar to that of paclitaxel, e.g. see Physician's Desk Reference, 49th Edition, Medical Economics, p 682, 1995. The dosage, mode and schedule of administration for the compound of this invention are not particularly restricted; an oncologist skilled in the art of cancer treatment will be able to ascertain, without undue experimentation, an appropriate treatment protocol for administering the compound of the present invention. Thus the compound of formula I may be administered via any suitable route of administration, parenterally or orally. Parenteral administration includes intravenous, intraperitoneal, intramuscular, and subcutaneous administration.

The doses utilized to implement the methods in accordance with the invention are the ones that make it possible to administer prophylactic treatment or to evoke a maximal therapeutic response. The doses vary, depending on the type of administration, the particular product selected, and the personal characteristics of the subject to be treated. In general, the doses are the ones that are therapeutically effective for the treatment of disorders caused by abnormal cell proliferation. The products in accordance with the invention can be administered as often as necessary in order to obtain the desired therapeutic effect. Some patients may respond rapidly to relatively high or low doses, and then require mild maintenance or no maintenance dose at all. Via the iv route, the dosage may be, for example, in the range of about 20 to about 500 mg/m$^2$ over 1 to 100 hours. Via the oral route, the dosage may be in the range of 5–1000 mg/kg/day of body weight. The actual dose used will vary according to the particular composition formulated, the route of administration, and the particular site, host and type of tumor being treated. Many factors that modify the action of the drug will be taken into account in determining the dosage including age, weight, sex, diet and the physical condition of the patient.

The present invention also provides pharmaceutical formulations (compositions) containing an antitumor effective amount of compound of formula I in combination with one or more pharmaceutically acceptable carriers, excipients, diluents or adjuvants. The compositions can be prepared in accordance with conventional methods. Examples of formulating paclitaxel or derivatives thereof may be found in, for example, U.S. Pat. Nos. 4,960,790 and 4,814,470, and such examples may be followed to formulate the compound of this invention. For example, compound of formula I may be formulated in the form of tablets, pills, powder mixtures, capsules, injectables, solutions, suppositories, emulsions, dispersions, food premix, and in other suitable forms. It may also be manufactured in the form of sterile solid compositions, for example, freeze dried and, if desired, combined with other pharmaceutically acceptable excipients. Such solid compositions can be reconstituted with sterile water, physiological saline, or a mixture of water and an organic solvent, such as propylene glycol, ethanol, and the like, or some other sterile injectable medium immediately before use for parenteral administration.

Typical of pharmaceutically acceptable carriers are, for example, manitol, urea, dextrans, lactose, potato and maize starches, magnesium stearate, talc, vegetable oils, polyalkylene glycols, ethyl cellulose, poly(vinylpyrrolidone), calcium carbonate, ethyl oleate, isopropyl myristate, benzyl benzoate, sodium carbonate, gelatin, potassium carbonate, silicic acid. The pharmaceutical preparation may also contain nontoxic auxiliary substances such as emulsifying, preserving, wetting agents, and the like as for example, sorbitan monolaurate, triethanolamine oleate, polyoxyethylene monostearate, glyceryl tripalmitate, dioctyl sodium sulfosuccinate, and the like.

What is claimed is:

1. A compound of formula I, or a pharmaceutically acceptable salt thereof

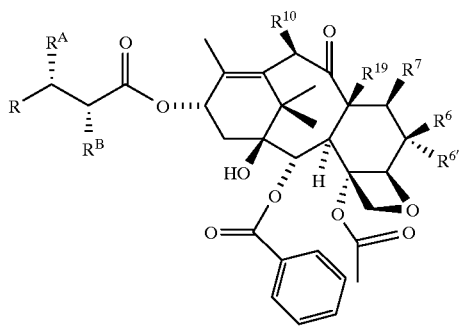

I wherein R is hydrogen, $C_{1-6}$ alkyl, $C_{2-6}$ alkenyl, $C_{2-6}$ alkynyl, $C_{3-6}$ cycloalkyl, $C_{3-6}$ cycloalkenyl, cyclic 3–7 membered ring containing either one or two heteroatoms, heteroaryl or —$Z^1$—$R^3$;

$Z^1$ is a direct bond, $C_{1-6}$ alkyl, or —O—$C_{1-6}$ alkyl;

$R^3$ is aryl, substituted aryl, $C_{3-6}$ cycloalkyl, $C_{3-6}$ cycloalkenyl, cyclic 3–7 membered ring containing either one or two heteroatoms, or heteroaryl;

$R^A$ is —NHC(O)R, —NHC(O)OR, —NHC(O)NHR, —NHC(O)N(R)$_2$, —NHS(O)$_m$R, —NHP(=O)(OR)$_2$, —NHP=S(OR)$_2$, where m is 1 or 2;

$R^B$ is hydroxy, fluoro, —OC(O)$R^x$, —OC(O)$OR^x$, OP(O)(OH)$_2$, OCH$_2$OP(O)(OH)$_2$, —OCH$_2$OCH$_2$OP(=O)(OH)$_2$, OP(O)(OH)$_2$ base, OCH$_2$OP(O)(OH)$_2$ base, —OCH$_2$OCH$_2$OP(=O)(OH)$_2$ base, —(OCH$_2$)$_m$OC=OCH$_2$NHR$^x$, —(OCH$_2$)$_m$OC(=O)CH(R")NR'$_6$R'$_7$ where m is 0–3, —OCOCH$_2$CH$_2$NH$_3^+$ HCOO$^-$, —OCOCH$_2$CH$_2$COOH, —OCO(CH$_2$)$_3$COOH,— OC(O)(CH$_2$)$_n$NR$^F$R$^G$, where n is 0–3, —OC(O)CH$_2$CH$_2$C(O)OCH$_2$CH$_2$OH or —OC(O)—Z—C(O)—R';

Z is ethylene (—CH$_2$CH$_2$—), propylene (—CH$_2$CH$_2$CH$_2$—), —CH=CH—, 1,2-cyclohexane or 1,2-phenylene;

R' is —OH, —OH base, —NR'$_2$R'$_3$, —OR'$_3$, —SR'$_3$ or —OCH$_2$C(O)NR'$_4$R'$_5$;

R'$_2$ is —H or —CH$_3$;

R'$_3$ is —(CH$_2$)$_n$NR'$_6$R'$_7$ or (CH$_2$)$_n$N$^+$R'$_6$R'$_7$R'$_8$X$^-$, where n is 1–3;

R'$_4$ is —H or —$C_1$–$C_4$ alkyl;

R'$_5$ is —H, —$C_1$–$C_4$ alkyl, benzyl, hydroxyethyl, —CH$_2$C O$_2$H or dimethylaminoethyl;

R'$_6$ and R'$_7$ are independently —H, —CH$_3$, —CH$_2$CH$_3$, benzyl or R'$_6$ and R'$_7$ together with the nitrogen of NR'$_6$R'$_7$ form a pyrrolidino, piperidino, morpholino, or N-methylpiperizino group;

R'$_8$ is —CH$_3$, —CH$_2$CH$_3$ or benzyl;

X$^-$ is halide;

base is NH$_3$, (HOC$_2$H$_4$)$_3$N, N(CH$_3$)$_3$, CH$_3$N(C$_2$H$_4$)$_2$NH, NH$_2$(CH$_2$)$_6$NH$_2$, N-methylglucamine, NaOH or KOH;

R$^F$ and R$^G$ are independently —H or —$C_1$–$C_3$ alkyl, or R$^F$ and R$^G$ taken together with the nitrogen of NR$^F$R$^G$ form a pyrrolidino, piperidino, morpholino or N-methylpiperizino groups;

R" is —H, —CH$_3$, —CH$_2$CH(CH$_3$)$_2$, —CH(CH$_3$)CH$_2$CH$_3$, —CH(CH$_3$)$_2$, —CH$_2$phenyl, —(CH$_2$)$_3$NH$_2$, —(CH$_2$)$_4$NH$_2$, —CH$_2$CH$_2$COOH, —(CH$_2$)$_3$NHC(=NH)NH$_2$, the residue of the amino acid proline, —OC(O)CH=CH$_2$, —C(O)CH$_2$CH$_2$C(O)NHCH$_2$CH$_2$SO$_3$—Y+ or —OC(O)CH$_2$CH$_2$C(O)NHCH$_2$CH$_2$CH$_2$SO$_3$—Y+;

Y+ is Na+ or N+ (Bu)$_4$;

$R^6$ and $R^{6'}$ are independently fluoro, chloro, bromo, iodo or ONO$_2$ with the proviso that one of $R^6$ or $R^{6'}$ is hydrogen;

$R^7$ is hydrogen, hydroxy, —O—$C_{1-6}$ alkyl, —OC(O)$R^x$, —OC(O)OR$^x$, —OC(O)NHR$^x$, —OC(O)NR'$_6$R'$_7$, —OCH$_2$OR, —OC(R$^x$)$_2$OR, —OCHR$^x$OR, —OCH$_2$OCH$_2$SCH$_3$, OP(O)(OH)$_2$, OCH$_2$OP(O)(OH)$_2$, —OCH$_2$OCH$_2$OP(O)(OH)$_2$, —(OCH$_2$)$_n$OC=OCH$_2$NHR$^x$, —(OCH$_2$)$_n$OC(=O)CH(R")NR'$_6$R'$_7$, where n is 0–3, OCH$_2$SR, —OC(R$^x$)$_2$SR, —OCHR$^x$SR, —OCOCH$_2$CH$_2$NH$_3^+$ HCOO$^-$, —OCOCH$_2$CH$_2$COOH, —OCO(CH$_2$)$_3$COOH,—OC(O)(CH$_2$)$_n$NR$^F$R$^G$, where n is 0–3, —OC(O)—Z—C(O)—R', —OC(O)CH$_2$CH$_2$C(O)OCH$_2$CH$_2$OH or when taken together with R$^{19}$ forms a cyclopropane ring;

R$^{19}$ is methyl or when taken together with $R^7$ forms a cyclopropane ring;

$R^{10}$ is hydrogen, hydroxy, —OC(O)R$^x$, —OC(O)OR$^x$, —O—$C_{1-6}$ alkyl, —OCH$_2$OCH$_3$, —OCH$_2$OCH$_2$OCH$_3$, —OCH$_2$OCH$_2$OCH$_2$CH$_3$, —OCH$_2$OCH$_2$CH$_2$OCH$_3$, —OCH$_2$OCH$_2$CH$_2$OH, —OCH$_2$SR, —OCH$_2$OCH$_2$SCH$_3$, —OC(O)NR'$_6$R'$_7$, $C_{1-6}$ alkyl, $-(CH_2)_3C(O)R^x$, $-(CH_2)_3C(O)OR^x$, $-(CH_2)_3CN$, $-OP(O)(OH)_2$, $-OCH_2OP(O)(OH)_2$, $-OCH_2OCH_2OP(O)(OH)_2$, $-(OCH_2)_nOC=OCH_2NHR^x$, $-(OCH_2)_nOC(=O)CH(R")NR'_6R'_7$, where n is 0–3, $-OCOCH_2CH_2NH_3^+$ HCOO$^-$, $-OCOCH_2CH_2COOH$, $-OCO(CH_2)_3COOH$, $-OC(O)-Z-C(O)-R'$, $-OC(O)(CH_2)_nNR^FR^G$ where n is 0–3, or $-OC(O)CH_2CH_2C(O)OCH_2CH_2OH$; and $R^x$ is $C_{1-6}$ alkyl, $C_{2-6}$ alkenyl, $C_{2-6}$ alkynyl, $C_{3-6}$ cyclo alkyl, any of which groups can be optionally substituted with one to six of the same or different halogen atoms or with one or more hydroxy groups.

2. A compound of claim 1 having the formula I, or a pharmaceutically acceptable salt thereof,

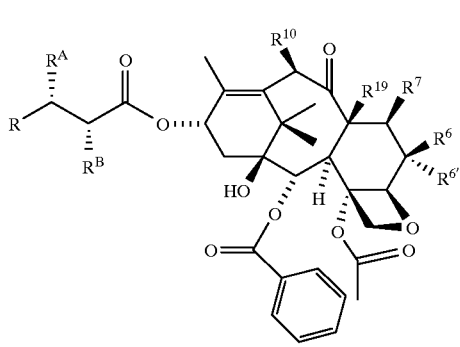

I wherein:

R is 2-furanyl (2-furyl), 2-thienyl, 3-furanyl (3-furyl), 3-thienyl, phenyl, napthyl, 4-hydroxyphenyl, 4-methoxyphenyl, 4-fluorophenyl, 4-trifluoromethylphenyl, 2-propynyl, benzyl, phenethyl, phenylethenyl, 3,4-dimethoxyphenyl, 2-(2-furanyl)ethenyl, 2-methylpropyl, $C_{3-6}$ cycloalkyl, cyclohexylmethyl, cyclohexylethyl, $C_{3-6}$ alkyl, $C_{3-6}$ alkenyl, t-butyl, or $-Z^1-R^3$;

$Z^1$ is a direct bond;

$R^3$ is aryl or substituted aryl;

$R^A$ is $-NHC(O)R$, $-NHC(O)OR$, $-NHC(O)NHR$, $-NHC(O)N(R)_2$, $-NHS(O)_mR$, $-NHP(=O)(OR)_2$, $-NHP=S(OR)_2$, where m is 1 or 2;

$R^B$ is hydroxy, fluoro, $-OC(O)R^x$, $-OC(O)OR^x$, OP(O)(OH)_2, OCH_2OP(O)(OH)_2, $-OCH_2OCH_2OP(=O)(OH)_2$, OP(O)(OH)_2 base, OCH_2OP(O)(OH)_2 base, $-OCH_2OCH_2OP(=O)(OH)_2$ base, $-(OCH_2)_mOC=OCH_2NHR^x$, $-(OCH_2)_mOC(=O)CH(R")NR'_6R'_7$ where m is 0–3, $-OCOCH_2CH_2NH_3^+$ HCOO$^-$, $-OCOCH_2CH_2COOH$, $-OCO(CH_2)_3COOH$, $-OC(O)(CH_2)_nNR^FR^G$, where n is 0–3, $-OC(O)CH_2CH_2C(O)OCH_2CH_2OH$ or $-OC(O)-Z-C(O)-R'$;

Z is ethylene ($-CH_2CH_2-$), propylene ($-CH_2CH_2CH_2-$), $-CH=CH-$, 1,2-cyclohexane or 1,2-phenylene;

R' is $-OH$, $-OH$ base, $-NR'_2R'_3$, $-OR'_3$, $-SR'_3$, or $-OCH_2C(O)NR'_4R'_5$;

$R'_2$ is $-H$ or $-CH_3$;

$R'_3$ is $-(CH_2)_nNR'_6R'_7$ or $(CH_2)_nN^+R'_6R'_7R'_8X^-$, where n is 1–3;

$R'_4$ is $-H$ or $-C_1-C_4$ alkyl;

$R'_5$ is $-H$, $-C_1-C_4$ alkyl, benzyl, hydroxyethyl, $-CH_2CO_2H$ or dimethylaminoethyl;

$R'_6$ and $R'_7$ are independently $-H$, $-CH_3$, $-CH_2CH_3$, benzyl or $R'_6$ and $R'_7$ together with the nitrogen of $NR'_6R'_7$ form a pyrrolidino, piperidino, morpholino, or N-methylpiperizino group;

$R'_8$ is $-CH_3$, $-CH_2CH_3$ or benzyl;

$X^-$ is halide;

base is $NH_3$, $(HOC_2H_4)_3N$, $N(CH_3)_3$, $CH_3N(C_2H_4)_2NH$, $NH_2(CH_2)_6NH_2$, N-methylglucamine, NaOH or KOH;

$R^F$ and $R^G$ are independently $-H$ or $-C_1-C_3$ alkyl, or $R^F$ and $R^G$ taken together with the nitrogen of $NR^FR^G$ form a pyrrolidino, piperidino, morpholino or N-methylpiperizino groups;

R" is $-H$, $-CH_3$, $-CH_2CH(CH_3)_2$, $-CH(CH_3)CH_2CH_3$, $-CH(CH_3)_2$, $-CH_2$phenyl, $-(CH_2)_3NH_2$, $-(CH_2)_4NH_2$, $-CH_2CH_2COOH$, $-(CH_2)_3NHC(=NH)NH_2$, the residue of the amino acid proline, $-OC(O)CH=CH_2$, $-C(O)CH_2CH_2C(O)NHCH_2CH_2SO_3-Y+$ or $-OC(O)CH_2CH_2C(O)NHCH_2CH_2CH_2SO_3-Y+$;

Y+ is Na+ or N+ (Bu)$_4$;

$R^7$ is hydrogen, hydroxy, $-O-C_{1-6}$ alkyl, $-OC(O)R^x$, $-OC(O)OR^x$, $-OC(O)NHR^x$, $-OC(O)NR'_6R'_7$, $-OCH_2OR$, $-OC(R^x)_2OR$, $-OCHR^xOR$, $-OCH_2OCH_2SCH_3$, $OP(O)(OH)_2$, $OCH_2OP(O)(OH)_2$, $-OCH_2OCH_2OP(O)(OH)_2$, $-(OCH_2)_nOC=OCH_2NHR^x$, $-(OCH_2)_nOC(=O)CH(R")NR'_6R'_7$, where n is 0–3, $-OCH_2SR$, $-OC(R^x)_2SR$, $-OCHR^xSR$, $-OCOCH_2CH_2NH_3^+$ HCOO$^-$, $-OCOCH_2CH_2COOH$, $-OCO(CH_2)_3COOH$, $-OC(O)(CH_2)_nNR^FR^G$, where n is 0–3, $-OC(O)-Z-C(O)-R'$, $-OC(O)CH_2CH_2C(O)OCH_2CH_2OH$ or when taken together with $R^{19}$ forms a cyclopropane ring;

$R^{19}$ is methyl or when taken together with $R^7$ forms a cyclopropane ring; and $R^{10}$ is hydrogen, hydroxy, $-OC(O)R^x$, $-OC(O)OR^x$, $-O-C_{1-6}$ alkyl, $-OCH_2OCH_3$, $-OCH_2OCH_2OCH_3$, $-OCH_2OCH_2OCH_2CH_3$, $-OCH_2OCH_2CH_2OCH_3$, $-OCH_2OCH_2CH_2OH$, $-OCH_2SR$, $-OCH_2OCH_2SCH_3$, $-OC(O)NR'_6R'_7$, $C_{1-6}$ alkyl, $-(CH_2)_3C(O)R^x$, $-(CH_2)_3C(O)OR^x$, $-(CH_2)_3CN$, $-OP(O)(OH)_2$, $-OCH_2OP(O)(OH)_2$, $-OCH_2OCH_2OP(O)(OH)_2$, $-(OCH_2)_nOC=OCH_2NHR^x$, $-(OCH_2)_nOC(=O)CH(R")NR'_6R'_7$, where n is 0–3, $-OCOCH_2CH_2NH_3^+$ HCOO$^-$, $-OCOCH_2CH_2COOH$, $-OCO(CH_2)_3COOH$, $-OC(O)-Z-C(O)-R'$, $-OC(O)(CH_2)_nNR^FR^G$ where n is 0–3, or $-OC(O)CH_2CH_2C(O)OCH_2CH_2OH$.

3. A compound of claim 2 wherein:

$R^B$ is hydroxy, $OP(O)(OH)_2$, $OCH_2OP(O)(OH)_2$, $-OCH_2OCH_2OP(=O)(OH)_2$, $OP(O)(OH)_2$ base, $OCH_2OP(O)(OH)_2$base or $-OCH_2OCH_2OP(=O)(OH)_2$ base;

$R^7$ is hydrogen, hydroxy, $-O-C_{1-6}$ alkyl, $-OC(O)R^x$, $-OC(O)OR^x$, $-OCH_2OR$, $-OC(R^x)_2OR$, $-OCHR^xOR$, $-OCH_2OCH_2SCH_3$, $OP(O)(OH)_2$, $OCH_2OP(O)(OH)_2$, $-OCH_2OCH_2OP(O)(OH)_2$, $OCH_2SR$, $-OC(R^x)_2SR$, $-OCHR^xSR$ or when taken together with $R^{19}$ forms a cyclopropane ring;

$R^{19}$ is methyl or when taken together with $R^7$ forms a cyclopropane ring; and $R^{10}$ is hydrogen, hydroxy, $-OC(O)R^x$, $-OC(O)OR^x$, $-O-C_{1-6}$ alkyl, $-OCH_2OCH_3$, —OCH$_2$OCH$_2$OCH$_3$, —OCH$_2$OCH$_2$OCH$_2$CH$_3$, —OCH$_2$OCH$_2$CH$_2$OCH$_3$, —OCH$_2$OCH$_2$CH$_2$OH, —OCH$_2$SR, —OCH$_2$OCH$_2$SCH$_3$, —(CH$_2$)$_3$C(O)R$^x$, —(CH$_2$)$_3$C(O)OR$^x$, —OP(O)(OH)$_2$, —OCH$_2$OP(O)(OH)$_2$ or —OCH$_2$OCH$_2$OP(O)(OH)$_2$.

4. A compound of claim 3, wherein

R$^A$ is —NHC(O)O—(C$_{1-6}$)alkyl, —NHC(O)OCH$_2$Ph, —NHC(O)Ph or NHC(O)-2-furyl;

R is phenyl, mono or di-substituted phenyl;

R$^{6'}$ is F, Cl, Br, I or ONO$_2$;

R$^{10}$ is —H, —OH or —OC(O)CH$_3$;

R$^B$ is hydroxy; and

R$^{19}$ is methyl.

5. A compound of claim 4, wherein

R$^A$ is —NHC(O)OtBu or —NHC(O)Ph;

R is phenyl;

R$^7$ is hydrogen, OH, —OC$_{1-6}$ alkyl, —OCH$_2$OC$_{1-6}$ alkyl or —OCH$_2$SC$_{1-6}$ alkyl; and R$^{10}$ is —OC(O)CH$_3$.

6. A compound of claim 5, wherein

R$^7$ is hydrogen, OH, —OCH$_3$, —OCH$_2$OCH$_3$ or —OCH$_2$SCH$_3$.

7. A compound of claim 5, wherein

R$^A$ is —NHC(O)Ph; and

R$^{6'}$ is F or Br.

8. A compound of claim 4 selected from the group consisting of compounds Ia–Is as identified below:

| Compd | R$^A$ | R | R$^6$ | R$^{6'}$ | R$^7$ | R$^{10}$ |
|---|---|---|---|---|---|---|
| Ia | —NHC(O)Ph | —Ph | —H | —F | —OH | —OC(O)CH$_3$ |
| Ib | —NHC(O)Ph | —Ph | —H | —F | —OCH$_2$OCH$_3$ | —OC(O)CH$_3$ |
| Ic | —NHC(O)Ph | —Ph | —H | —F | —OCH$_2$SCH$_3$ | —OC(O)CH$_3$ |
| Id | —NHC(O)Ph | —Ph | —H | —F | —OCH$_3$ | —OC(O)CH$_3$ |
| Ie | —NHC(O)Ph | —Ph | —H | —Br | —OH | —OC(O)CH$_3$ |
| If | —NHC(O)Ph | —Ph | —H | —ONO$_2$ | —OH | —OC(O)CH$_3$ |
| Ig | —NHC(O)Ph | —Ph | —H | —ONO$_2$ | —OCH$_2$OCH$_3$ | —OC(O)CH$_3$ |
| Ih | —NHC(O)Ph | —Ph | —H | —ONO$_2$ | —OCH$_2$SCH$_3$ | —OC(O)CH$_3$ |
| Ij | —NHC(O)Ph | —Ph | —H | —Cl | —OH | —OC(O)CH$_3$ |
| Ik | —NHC(O)OC(CH$_3$)$_3$ | —Ph | —H | —F | —OH | —OC(O)CH$_3$ |
| Il | —NHC(O)OC(CH$_3$)$_3$ | —Ph | —H | —F | —OCH$_2$OCH$_3$ | —OC(O)CH$_3$ |
| Im | —NHC(O)OC(CH$_3$)$_3$ | —Ph | —H | —F | —OCH$_2$SCH$_3$ | —OC(O)CH$_3$ |
| In | —NHC(O)OC(CH$_3$)$_3$ | —Ph | —H | —F | —OCH$_3$ | —OC(O)CH$_3$ |
| Io | —NHC(O)Ph | —Ph | —Cl | —H | —H | —OC(O)CH$_3$ |
| Ip | —NHC(O)Ph | —Ph | —Br | —H | —H | —OC(O)CH$_3$ |
| Iq | —NHC(O)Ph | —Ph | —I | —H | —H | —OC(O)CH$_3$ |
| Ir | —NHC(O)OC(CH$_3$)$_3$ | —Ph | —Cl | —H | —H | —OC(O)CH$_3$ |
| Is | —NHC(O)OCH(CH$_3$)$_2$ | —Ph | —Cl | —H | —H | —OC(O)CH$_3$ |

9. A pharmaceutical formulation which comprises an antitumor effective amount of a compound of formula I as claimed in any one of claims 1–8.

10. A method for inhibiting tumor growth in a mammalian host which comprises administering to said mammal a tumor-growth inhibiting amount of a compound of formula I as claimed in any one of claims 1–8.

\* \* \* \* \*